US 7,604,935 B2

(12) United States Patent
Upmeier et al.

(10) Patent No.: US 7,604,935 B2
(45) Date of Patent: Oct. 20, 2009

(54) SOLUBLE RUBELLA E1 ENVELOPE PROTEIN VARIANTS

(75) Inventors: Barbara Upmeier, Iffeldorf (DE); Ralf Bollhagen, Penzberg (DE); Alfred Engel, Tutzing (DE); Elke Faatz, Huglfing (DE); Peter Schaarschmidt, Uffing (DE); Christian Scholz, Penzberg (DE); Toralf Zarnt, Iffeldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 265 days.

(21) Appl. No.: 11/584,887

(22) Filed: Oct. 23, 2006

(65) Prior Publication Data

US 2007/0154883 A1     Jul. 5, 2007

(30) Foreign Application Priority Data

Oct. 26, 2005    (EP)     .................................. 05109993

(51) Int. Cl.
    *C12Q 1/70*       (2006.01)
    *C12N 7/01*       (2006.01)
    *A61K 39/20*      (2006.01)

(52) U.S. Cl. .................. 435/5; 435/7.1; 435/219.1; 435/235.1; 530/826

(58) Field of Classification Search ................ None
See application file for complete search history.

(56) References Cited

U.S. PATENT DOCUMENTS 6,645,732 B2    11/2003    Faatz et al.

FOREIGN PATENT DOCUMENTS

| EP | 0 061 888 | 10/1982 |
|---|---|---|
| EP | 0061888 B1 | 10/1982 |
| EP | 0 299 673 | 1/1989 |
| EP | 0299673 | 1/1989 |
| EP | 0944838 B1 | 9/1999 |
| WO | WO 98/13496 | 4/1998 |
| WO | WO 98/23961 | 6/1998 |
| WO | WO 03/000877 | 1/2003 |
| WO | WO 03/000877 A2 | 1/2003 |
| WO | WO 03/000878 | 1/2003 |
| WO | WO 03/000878 A2 | 1/2003 |

OTHER PUBLICATIONS

Seto, N., et al., "Expression and Characterization of a Soluble Rubella Virus E1 Envelope Protein", Journal of Medical Virology, vol. 44, 1994, pp. 192-199.

Starkey, William G., et al., "Use of Rubella Virus E1 Fusion Proteins for Detection of Rubella Virus Antibodies", Journal of Clinical Microbiology, Feb. 1995, pp. 270-274.

Gros, Christof, et al., "Analyses of Disulfides Present in the Rubella Virus E1 Glycoprotein", Virology, vol. 230, 1997, pp. 179-186.

(Continued)

*Primary Examiner*—Mary E Mosher
*Assistant Examiner*—Stuart W Snyder
(74) *Attorney, Agent, or Firm*—Barnes & Thornburg LLP

(57) ABSTRACT

A soluble rubella E1 antigen variant is disclosed that comprises amino acids 334-409 of the native rubella E1 peptide, but lacks the C-terminal end and at least the transmembrane region and the anchor segment as well as at least the amino acids 143 to 164. Also described is a recombinant DNA molecule encoding the rubella E1 antigen variants which are recombinantly expressed as a chaperone fusion protein, refolded into a soluble and immunoreactive conformation, and further used for the serological detection of anti-rubella antibodies. In addition, also disclosed is a method for the detection, determination and quantification of anti-rubella antibodies of IgG and/or IgM subclass in a sample wherein the rubella E1 antigen is used as a capture reagent and/or binding partner for the antibodies.

16 Claims, 2 Drawing Sheets

OTHER PUBLICATIONS

Baron, Michael D., et al., "Oligomerisation of the Structural Proteins of Rubells Virus", Virology, vol. 185, 1991, pp. 811-819.
Buchner, Johannes "Supervising the Fold: Functional Principles of Molecular Chaperones", The FASEB Journal, vol. 10, Jan. 1996, pp. 10-19.
Chaye, Helena, et al., "Human T- and B-Cell Epitopes of E1 Glycoprotein of Rubella Virus", Journal of Clinical Immunology, vol. 13 No. 2, 1993, pp. 93-100.
Giebauf, Andreas, et al. "A Synthetic Peptide ELISA for the Screening of Rubella Virus Neutralizing Antibodies in Order to Ascertain Immunity", Journal of Immunological Methods, vol. 287, 2004 pp. 1-11.
Green, Kim Y., et al. "Rubella Virus Antigens: Localization of Epitopes Involved in Hemagglutination and Neutralization by Using Monoclonal Antibodies", Journal of Virology, Mar. 1986, pp. 893-898.
Hobman, Tom C., et al. "Assembly of Rubella Virus Structural Proteins into Virus-like Particles in Transfected Cells", Virology, vol. 202, 1994, pp. 574-585.
Ho-Terry, Linda, et al., "Rubella Virus Haemagglutinin: Association with a Single Virion Glyeoprotein", Archives of Virology, vol. 84, 1985, pp. 207-215.
Hottenrott, Sandra, et al., "The *Escherichia coli* SlyD is a Metal Ion-regulated Peptidyl-prolyl cis/trans-Isomerase", The Journal of Biological Chemistry, vol. 272, No. 25, 1997, pp. 15697-15701.
Mitchell, Leslie Ann, et al., "Identification of Immunoreactive Regions of Rubella Virus E1 and E2 Envelope Proteins by Using Synthetic Peptides", Virus Research, vol. 29, 1993, pp. 33-57.
Mitterauer, Thomas, et al., "Metal-Dependent Nucleotide Binding to the *Escherichia coli* Rotamase SlyD", Biochem. J., vol. 342, 1999, pp. 33-39.
Mukherjee, Sourav, et al., "Single-Step purification of a Protein-Folding Catalyst, The SlyD Peptidyl Prolyl Isomerase (PPI), from Cytoplasmic Extracts of *Exchericia coli*", Biotechnol. Appl. Biochem., vol. 37, 2003, pp. 183-186.
Newcombe, Jane, et al., "Recombinant Rubella E1 Fusion Proteins for Antibody Screening and Diagnosis", Clinical and Diagnostic Virology, vol. 2, 1994, pp. 149-163.
Oker-Blom, Christian, et al., "Rubella Virus 40S Genome RNA Specifies a 24S Subgenomic mRNA That Codes for a Precursor to Structural Proteins", Journal of Virology, Feb. 1984, pp. 403-408.
Qiu, Zhiyong, et al., "Expression and Characterization of Virus-Like Particles Containing Rubella Virus Structural Proteins" Journal of Virology vol. 68 No. 6 Jun. 1994 pp. 4086-4091.
Ramm, Kathrin, et al., "The Periplasmic *Escherichia coli* Peptidylprolyl cis, Trans-Isomerase FkpA", The Journal of Biological Chemistry, vol. 275, No. 22, Jun. 2000, pp. 17106-17113.
Scholz, Christian, et al., "Cooperation of Enzymatic and Chaperone Functions of Trigger Factor in the Catalysis of Protein Folding", The EMBO Journal vol. 16, No. 1, 1997 pp. 54-58.
Scholz, Christian, et al., "Functional Solubilization of Aggregation-Prone HIV Envelope Proteins by covalent fusion with Chaperone Modules", J. Mol. Biol. vol. 345, 2005, 1229-1241.
Seppanen, Helena, et al., "Diagnositc Potential of Baculovirus-Expressed Rubella Virus Envelope Proteins", Journal of Clinical Microbiology, vol. 29, No. 9, Sep. 1991, pp. 1877-1882.
Terry, G. M., et al., "Rubella Virus RNA: Effect of High Multiplicity Passage", Archives of Virology, vol. 86, 1985, pp. 29-36.
Terry, G. M., et al., "Localization of the Rubella E1 Epitopes", Arch. Virol. ,vol. 98, 1988, pp. 189-197.
"Preparation of Enzyme—Antibody or Other Enzyme—Macromolecule Conjugates", Practise and Theory of Enzyme Immuno assays, Marcomolecule Conjugation, Chapter 11, pp. 221-278.
Waxham, M. Neal, et al., "Immunochemical Identification of Rubella Virus Hemagglutinin", Virology, vol. 126, 1983, pp. 194-203.
Waxham, M. Neal, et al., "A Model of the Structural Organization of Rubella Virions", Reviews of Infectous Diseases, vol. 7, Supp. 1, Mar.-Apr. 1985, pp. S133-S139.

Wolinsky, Jerry S., et al., "Monoclonal Antibody-Defined Epitope Map of Expressed Rubella Virus Protein Domains", Journal of Virology, Aug. 1991, pp. 3986-3994.
Wolinsky, Jerry S., "Rubella", Fields Virology, Third Edition, chapter 29, 1996, pp. 899-929.
Baron, M. et al., "Oligomerisation of the Structural Proteins of Rubella Virus," Virology 185, 811-819 (1991).
Buchner, J., "Supervising the fold: functional principles of molecular chaperones," The FASEB Journal, vol. 10, Jan. 1996, 10-19.
Chaye, H. et al., "Human T- and B-Cell Epitopes of E1 Glycoprotein of Rubella Virus," Journal of Clinical Immunology, vol. 13, No. 2, 1993, 93-100.
Gießauf, A. et al., "A synthetic peptide ELISA for the screening of rubella virus neutralizing antibodies in order to ascertain immunity," Journal of Immunological Methods 287(2004) 1-11.
Green, K. et al., "Rubella Virus Antigens: Localization of Epitopes Involved in Hemagglutination and Neutralization by Using Monoclonal Antibodies," Journal of virology, Mar. 1986, vol. 57, No. 3, 893-898.
Gros, C. et al., "Analyses of Disulfides Present in the Rubella Virus E1 Glycoprotein," Virology 230, 179-186(1997).
Hobman, T. et al., "Assembly of Rubella Virus Structural Proteins into virus-like Particles in Transfected Cells," Virology 202, 574-585 (1994).
Mitchell, L. et al.' "Identification of immunoreactive regions of rubella virus E1 and E2 envelope proteins by using synthetic peptides," Virus Research, 29(1993) 33-57.
Mitterauer, T. et al., "Metal-dependent nucleotide binding to the *Escherichia coli* rotamase SlyD," Biochem. J. (1999) 342,33-39.
Mukherjee, S. et al., "Single-step purification of a protein-folding catalyst, the SlyD peptidyl prolyl isomerase (PPI), from cytoplasmic extracts of *Escherichia coli*," Biotechnol. Appl. Biochem. (2003) 37, 183-186.
Newcombe, J. et al., "Recombinant rubella E1 fusion proteins for antibody screening and diagnosis," Clinical and Diagnostic Virology, 2(1994) 149-163.
Oker-Blom, C. et al., "Rubella Virus 40S Genome RNA Specifies a 24S Subgenomic mRNA that Codes for a Precursor to Structural Proteins," Journal of Virology, vol. 49, No. 2, Feb. 1984, 403-408.
Oker-Blom, C. et al., "Rubella Virus Contains One Capsid Protein and Three Envelope Glycoproteins, E1, E2a, and E2b," Journal of Virology, vol. 46, No. 3, Jun. 1983, 964-973.
Qiu, Z. et al., "Expression and Characterization of Virus-Like Particles Containing Rubella Virus Structural Proteins," Journal of Virology, vol. 68, No. 6, Jun. 1994, 4068-4091.
Ramm, K. et al., "The Periplasmic *Escherichia coli* Peptidylprolyl cis, trans-Isomerase FkpA," The Journal of Biological Chemistry, vol. 275, No. 22, Jun. 2, 2000, 17106-17113.
Scholz, C. et al., "Cooperation of enzymatic and chaperone functions of trigger factor in the catalysts of protein folding," The EMBO Journal, vol. 16, No. 1, 1997, 54-58.
Scholz, C. et al., "Functional Solubilization of Aggregation-prone HIV Envelope Protein by Covalent Fusion with Chaperone Modules," J. Mol. Biol. (2005) 1-13.
Seppanen, H. et al., "Diagnostic Potential of Baculovirus-Expressed Rubella Virus Envelope Protiens," Journal of Clinical Microbiology, vol. 29, No. 9, Sep. 1991, 1877-1882.
Starkey, W. et al., "Use of Rubella Virus E1 Fusion Proteins for Detection of Rubella Virus Antibodies," Journal of Clinical Microbiology, vol. 33, No. 2, Feb. 1995, 270-274.
Terry, G. et al., "A bio-engineered rubella E1 antigen," Arch. Virol. (1989) 104: 63-75.
Terry, G. et al., "Localization of the rubella E1 epitopes," Arch Virol (1988) 98: 189-197.
Ho-Terry, L, "Rubella Virus Haemagglutinin: Association with a Single Virion Glycoprotein," Archives of Virology 84, 207-215(1985).
Terry, G. et al., "Rubella Virus RNA: Effect of High Multiplicity Passage," Archives of Virology 86, 29-36(1958).
Waxham, M. et al., "A Model of the Structural Organization of Rubella Virions," Reviews of Infectious Diseases, vol. 7, Supplement 1, Mar.-Apr. 1985, S133-S139.

Waxham, M. et al., "Detailed immunologic analysis of the structural polypeptides of rubella virus using monoclonal antibodies," Virology, May 1985; 143(1) 153-65.

Wahxam, M. et al., "Immunochemical identification of rubella virus hemagglutinin," Virology, Arpil 1983I 126(1): 194-203.

Weber, B., "Current developments in the laboratory diagnosis of rubella," Bull Soc Sci Med Grand Duche Luxemb. 1997; 134(2): 31-41.

Wolinsky, J. et al., "Monoclonal Antibody-Defined Epitope Map of Expressed Rubella Virus Protein Domains," Journal of Virology, Aug. 1991, vol. 65, No. 8, 3986-3994.

Wolinsky, J. et al., "Rubella," Fields Virology, Third Edition (1996) Raven Publishers, Philadelphia.

Atherton, E. et al., "Solid phase peptide synthesis," IRL Press Oxford, UK 1989.

SOLUBLE RUBELLA E1 ENVELOPE PROTEIN VARIANTS

RELATED APPLICATIONS

This application claims priority to European application EP 05109993.5 filed Oct. 26, 2005.

FIELD OF THE INVENTION

The invention relates to a soluble rubella E1 antigen and variants of this peptide characterized by lacking at the C-terminal end at least the transmembrane region and the anchor segment as well as at least the amino acids 143 to 164 and containing at least the region spanning the disulfide bridges Cys 349-Cys 352 and Cys 368-40 1 whereas the N-terminus (Cys 349) of this region contains additionally at least 15 amino acids and/or the C-terminus (Cys 401) of this region contains additionally at least 8 amino acids of the adjacent rubella E1 antigen sequence. The N-terminus of this region (Cys 349) contains additionally at least 25, 30, 34 amino acids and/or the C-terminus (Cys 401) of this region contains additionally at least 10, 11, 15, 25, 35 amino acids of the adjacent rubella E1 antigen sequence.

BACKGROUND OF THE INVENTION

The rubella virus (RV) is a togavirus and the sole representative of the Rubivirus subgroup. The small enveloped virus has a size of 65 nm and consists of a 10 kb single-stranded RNA molecule encapsulated in an icosahedral nucleocapsid which is surrounded by a lipid envelope. The rubella virus causes a relatively mild childhood disease (German measles) which usually results in permanent immunity thought to be mediated by both T-lymphocytes and antibodies. Possible consequences of rubella infections in adults are transient/chronic arthritis, musculoskeletal syndromes, insulin-dependent diabetes mellitus and late onset of neurologic sequelae.

The rubella virus is a main parameter during early pregnancy. The specific detection of anti-rubella IgM and/or anti-rubella IgG, respectively, is crucial for the clarification if an acute infection or a blazing reinfection occurred.

Maternal rubella virus infection during pregnancy is associated with a risk of congenital rubella syndrome (CRS) in the fetus, the incidence of congenital malformations being highest when primary infection occurs in the first 12 weeks of gestation. For this reason the prevention of congenital abnormalities caused by RV infection during early pregnancy requires the determination of an individual's immune status by serology, which means a selective determination of IgG and IgM antibodies specific for rubella virus antigens. Primary rubella infection is associated with a specific IgM antibody response, while elevated levels of IgG in the absence of detectable IgM indicate an immune status which is protective against acute rubella virus infection.

When prenatal screening indicates that a woman has acquired a primary rubella infection during early stage of pregnancy, a therapeutic abortion is often recommended. As a result, it is imperative that the test results are accurate.

For detecting antibodies to RV the routine laboratory diagnosis is mainly based on ELISA (enzyme-liked immunoabsorbent assay) tests, while the most widely accepted method for determination of RV immune status in central Europe is the hemagglutination inhibition (HAI) test for the verification of the RV-IgG ELISA (Weber et al., Bull Soc Sci Med Grand Duche Luxemb. (1997), 31-41).

The detection of specific antibodies of a certain immunglobulin class can be performed by binding the immunoglobulin to a solid phase to which to specific antigen has been immobilized. The bound immunoglobulin is subsequently detected by a labeled antibody specific for human imunoglobulins of a certain class. This assay format can only be carried out by a two step assay format allowing a washing step which eliminated unbound immunoglobulins prior to detection. A one-step assay format often realized in automatic immunoassay analyzers requires the direct assay format of a double antigen sandwich, i.e. the specific antibody forms an immunocomplex binding to a first antigen which is immobilized to a solid phase or will mediate immobilization to a solid phase and to a second antigen carrying a label thus allowing quantitative or qualitative detection of the specifically bound antibody.

The selective determination of specific IgG antibodies in the presence of IgM antibodies of the same specificity in a one-step double antigen sandwich format strictly requires the use of soluble, monomeric or defined oligomeric antigens (EP 944,838), which reveals an immunoreactive conformation.

The rubella virus harbors four structural proteins which have been shown to be antigenic in animals and humans. These are the three envelope glycoproteins E1 (58 kDa), E2a (47 kDa) and E2b (42 kDa) and the non-glycosylated capsid (C) protein (33kDa) decorating the single RNA plus strand which constitutes the viral genome (Waxham and Wolinsky, Rev Infect Dis. (1985) 133-9; Oker-Blom et al., J Virol. 1984 (2):403-8).

It was shown that E2a and E2b are variants of the same gene product and the difference in migration in polyacrylamide gels is due to heterogenous glycosylation of the proteins. E1 and E2 have been found to form monomers or disulfide-linked complexes (E1-E1 and E1-E2), whereas C exists exclusively as a homodimer (Waxham and Wolinsky, Virology. (1983) 126 (1), 194-203; Wolinsky et al., Rubella (1996) Fields Virology. Lippincott-Raven Publisher, Philadelphia, 899-929). An extensive review of the biological, physical and biochemical properties of RV as well as the clinical features of the infection has been published by Wolinsky (1996).

At present, antigens are used for the detection of a rubella infection, which are derived from stably infected/transfected cell-lines and, in general, stem from eucaryotic overproduction. Seppanen et al., J. Clin. Microbiol (1991) 1877-1882 describes the expression of E1 and E2 of the rubella virus in *Spodoptera frugiperda* Sf9 insect cells by using the baculovirus expression system. Furthermore, a stably transfected CHO cell line expressing and secreting the structural proteins E1, E2 and C of RV in the form of RV-like particles (RLPs) is disclosed in Hobman et al., 1994 (574-585) Virology.

Rubella-like particles are composed of the rubella mainantigens E1, E2 and C, which are expressed as a viral polypeptide precursor protein. Due to signal sequences this unprocessed precursor protein is secreted into the media and virus-like particles are formed. The surface of these RLPs presents epitopes suited for the immunological detection of anti-RV antibodies in rubella-positive sera. The expression of noninfectious RV-like particles (VLPs) containing the three structural proteins of RV in BHK (baby hamster kidney cells) cell line is outlined in Qui et al., Journal of virology 1994 (4086-4091).

However, producing RV-antigens in eucarotic cell systems is labour intensive and time consuming, while the yield is comparatively low. Establishing of in vitro diagnostic methods of anti-rubella virus antibody detection requires procedures of producing recombinant RV antigens from procaryotic organisms like *E. coli* in a defined, soluble, functional, and reproducible quality with clear advantages compared to the established RLPs.

Although the know-how in the field of protein-design and engineering is strongly increasing, the rubella antigens E1, E2 and C are expressed with very low abundance in *E. coli* host cells and, moreover, they are poorly soluble.

The immuno-dominant rubella antigen, i.e. the antigen of choice for the immunological detection of antibodies from human sera, is the envelope-protein E1. The overall topology of the E1 protein comprises a large extracellular ectodomain (1-452) including an—helical region (438-452) with a transmembrane domain (453-468) followed by a short C-terminal anchor-segment (until 481).

One reason for the insolubility of E1 of RV could be due to the conformation of the ectodomain which is supposed to be stabilized by ten disulfide bridges. The rubella E1 peptide is organized into an amino-terminal (N-terminal) region and a carboxy-terminal (C-terminal) region with an overall content of 24 cysteine residues.

In general, the N-terminal end refers to the extremity of a protein or polypeptide terminated by an amino acid with a free amine group ($NH_2$), while the C-terminal end refers to the extremity of a protein or polypeptide terminated by an amino acid with a free carboxyl group (COOH).

Gros et al., (1997) disclose that the N-terminal region of the rubella E1 protein contains eight disulfides constructed from the cysteine residues C(8) to C(287), while the C-terminal region contains two disulfides generated from the cysteine residues C(249) to C(401). The residues C(456), C(466), and C(468) are located in the predicted transmembrane segment, and residue C(470) is predicted to be located in the interior of the virus. These data indicate that the residues C(456) to C(470) are not involved in disulfide formation.

The wealth of cysteine residues with the concomitant likelihood of false bridging events (intramolecular and intermolecular SH-shuffling is very probable to occur) suggests that the conformational and oxidative refolding of E1 is an extremely complex process which is difficult to control in vitro. Therefore, there is an urgent need for a simple and reliable protocol which facilitates both purification and high-yield refolding of the rubella antigens into an immunoreactive (i. e. antigenic) conformation. Native-like folded recombinant E1 envelope variants are a mandatory requirement to achieve a reliable immunoassay for antibodies against RV.

The rubella E1 ectodomain (1-452) contains 20 cysteine-residues. Their correct bridging determines the three-dimensional structure and is crucial for the exposition of the correct, native-like conformational epitopes. The oxidative refolding of cysteine-rich proteins, that is the formation of the correct intramolecular and/or intermolecular disulfide bridges, is a complex and experimentally demanding process. For the insertion of disulfide bridges in vivo into de-novo-synthesized or translocated proteins an arsenal of folding helpers (chaperones, oxido reductases, prolyl isomerases) are available in cell compartments (endoplasmic reticulum in eucaryotic, periplasm in procaryotic cells). Since the redox potential of the bacterial cytosol is strongly reducing (−270 mV), the cysteines of heterologous target proteins naturally occur as thiol moieties. When the expression is very high, the target proteins are deposited in the host cell as insoluble aggregates (the so-called inclusion bodies, IB).

Usually, the partially refolded and unfolded protein-fraction is solubilized under reducing conditions (e.g. 5 mM TCEP) in chaotropic solutions (7.0 M GdmCl, 8.0 M urea) resulting in unfolded protein chains, which have to be renatured (i.e. refolded into the native or a native-like conformation). As a general rule the yield of native-like folded protein is strongly decreased by incorrect disulfide bridges.

Disregarding conformational aspects, even limited numbers of cysteines (and the assumption of strictly intramolecular bridging events) yield huge numbers of erroneous bridging events ending up in unproductive side reactions like aggregation processes.

Different from in-vitro-refolding in a test tube, a huge arsenal of folding helpers in an optimized redox ambience as folding-assistance are available for the de novo folding in vivo. Nevertheless, the soluble expression of functional cysteine-rich proteins in procaryotic host cells like *E. coli* is still very complex. The aim to enhance the overproduction rate of immunoreactive antigens of RV and to increase the solubility of the refolded proteins has been achieved only to a limited extent.

In Newcombe et al., Clin Diagn Virol. 1994 (3)149-63, nine gluthatione-S-transferase (GST) E1 fusion proteins were used to express rubella E1 antigen-fragments in *E. coli* in a soluble form. Only after a substantial truncation of the E1 sequence a successful soluble expression was possible for the cysteine-free region 243-286 (44 amino acid residues). EP 299,673 discloses a peptide from amino acid residues 207-353 which retains rubella Ig specific binding characteristics.

Furthermore, Starkey et al., J. Clin. Microbiol. (1995), 270-274) disclose that only a very narrow area of 44 to 75 amino acid residues of a GST-E 1 fusion protein were soluble. GST fusion proteins containing the entire E1 coding sequence and larger subfragments were expressed in forms which could not be purified and were therefore presumed to be expressed as insoluble inclusion bodies.

In order to identify immunoreactive determinants within RV antigens, the E1 and E2 epitopes have been mapped extensively in the past years by using synthetic peptides (Mitchell et al., Virus Research 29(1993), 33-54). In addition, distinct independent epitopes have been located within RV E1 protein including domains that are important for viral infectivity and hemagglutination (Waxham and Wolinsky, Virology (1985) 153-65, Green and Dorsett, J. Virol. (1986) 57, 893-898, Ho-Terry et al., Arch Virol. 1985; 84 (3-4):207-15. The recombinant protein A-El-fusions described by Teffy et al, Arch Virol. (1988), 98, 189-97, characterized solely linear epitopes. The closer localization of epitopes of RV E1 glycoprotein is described by Terry et al., (1988), Wolinsky et al., J Virol. (1991), 3986-94, and Chaye et al., J Clin Immunol. 1993 Mar; 13(2) 93-100. Furthermore, Gieβauf et al., J. Immun. Meth. 287 (2004), 1-11, evaluate an ELISA by using several coated peptides of E1 to improve the determination of immunity against rubella. Only one of these peptides, the BCH-178 peptide, seemed to be successful for screening neutralizing antibodies as an additional method to confirm low positive or borderline HAI titres or RV-IgG values. There is no further proof that the small BCH-178 peptide (amino acid residues 213-239) contains most of the antigenic epitopes of the native E1 molecule (SEQ ID NO: 4). However, no reference has been made until now for the localization of the main reactivity of the immundominant rubella E1 envelope protein.

It was the aim of the present invention to provide a soluble rubella E1 variant from procariotic cell systems, which reconciles high solubility and high immunological reactivity in a serological assay.

SUMMARY OF THE INVENTION

The object of the present invention is a soluble rubella E1 antigen and variants of this peptide characterized by lacking at the C-terminal end at least the transmembran region and the anchor segment as well as at least the amino acids 143 to 164 and containing at least the region spanning the disulfide bridges Cys 349-Cys 352 and Cys 368-401 whereas the N-terminus (Cys 349) of this region contains additionally at least 15 amino acids and/or the C-terminus (Cys 401) of this region contains additionally at least 8 amino acids of the adjacent rubella E1 antigen sequence.

The region spanning the disulfide bridges Cys 349-Cys 352 and Cys 368-401 contains at the N-terminus of this region (Cys 349) additionally at least 25, 30, 34 amino acids and/or at the C-terminus (Cys 401) of this region additionally at least 10, 11, 15, 25, 35 amino acids of the adjacent rubella E1 antigen sequence.

The soluble rubella E1 antigen is further characterized by lacking at the C-terminal end additionally the α-helical region between amino acids residues 438 to 452.

Furthermore, the soluble rubella E1 antigen is characterized by the N-terminal region containing at least the region spanning the disulfide bridges Cys 8-Cys 13 and Cys 59-Cys 71, more preferably the disulfide bridge combination Cys 8-Cys 13 and Cys 59-Cys 71 and Cys 117-Cys 130.

Moreover, the soluble rubella E1 antigen is characterized by the C-terminal region containing at least the region spanning the disulfide bridges Cys 349-Cys 352 and Cys 368-Cys 401, more preferably the combination of the disulfide bridges Cys 225-Cys 235, Cys 349-Cys 352 and Cys 368-Cys 401 or the combination of the disulfide bridges Cys 176-Cys 185, Cys 349-Cys 352 and Cys 368-Cys 401, most preferably the combination of the disulfide bridges Cys 176-Cys 185, Cys 225-Cys 235, Cys 349-Cys 352 and Cys 368-Cys 401.

In addition, the invention relates to a recombinant DNA molecule, encoding a rubella E1 antigen and variants, which are recombinantly expressed as a chaperone fusion protein, refolded into a soluble and immunoreactive conformation and further used for the serological detection of anti-rubella antibodies.

The present invention discloses a method for the detection, determination and quantification of anti-rubella antibodies of IgG and/or IgM subclass in a sample wherein the rubella E1 antigen is used as a capture reagent and/or binding partner for the antibodies. The invention comprises further a diagnostic test and a reagent kit for the detection of anti-rubella antibodies, containing at least one antigen of the rubella E1 antigens.

BRIEF DESCRIPTION OF THE DRAWINGS

FIG. 1 shows an UV spectrum of the fusion protein SS-E1 (201-432) after matrix-assisted refolding and imidazole gradient elution. See Example 3a.

DETAILED DESCRIPTION OF THE INVENTION

Figure 1:
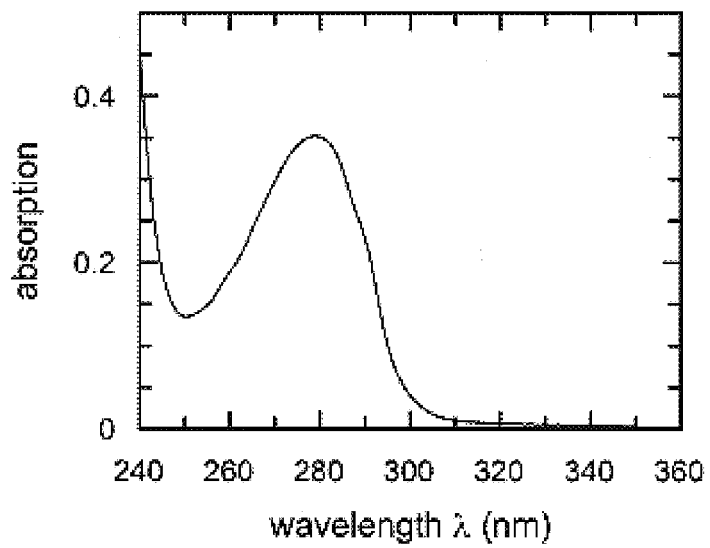

The invention discloses a soluble rubella E1 antigen and variants of this peptide characterized by lacking at the C-terminal end at least the transmembrane region and the anchor segment as well as at least the amino acids 143 to 164 and containing at least the region spanning the disulfide bridges Cys 349-Cys 352 and Cys 368-401 whereas the N-terminus (Cys 349) of this region contains additionally at least 15 amino acids and/or the C-terminus (Cys 401) of this region contains additionally at least 8 amino acids of the adjacent rubella E1 antigen sequence.

Furthermore, the region spanning the disulfide bridges Cys 349-Cys 352 and Cys 368-401 contains at the N-terminus (Cys 349) of this region additionally at least 25, 30, 34 amino acids and/or the C-terminus (Cys 401) of this region additionally at least 10, 11, 15, 25, 35 amino acids of the adjacent rubella E1 antigen sequence. The above described definition of amino acids which are necessary for the minimal requirement of the rubella E1 antigen are not absolute and can easily be verified by experiments by an average man skilled in the art.

The soluble rubella E1 antigen and variants of this peptide lacks preferably the amino acids 143 to 164, more preferable the N-terminus (amino acids 143) of this region lacks additionally at least 1, 2, 5, and/or at least 10 amino acids and/or the C-terminus (amino acids 164) of this region lacks additionally at least amino acids 1, 2, 5, and/or at least 10 amino acids of the adjacent rubella E1 antigen sequence. As the skilled artisan will appreciate the above described boundaries are use to indicate for certain range of amino acid residues lacking within the sequence of the rubella E1 protein. The above described definition of the boundaries is not absolute, the amount of amino acid residues lacking within this region is variable.

Moreover, the present invention further relates to a soluble recombinant rubella E1 antigen and variants of this peptide lacking additionally the α-helical region between amino acid residues 438 to 452.

To evaluate if it is possible to reduce the complexity of oxidative and conformational refolding of rubella E1 protein by substitution of certain cysteine residues and removal of certain sequences with extremely hydrophobic segments a deletion-analysis has been performed.

According to the present invention the term "disulfide bridge" relates to two cysteine residues which are adjacent in the three-dimensional structure of a protein and which can be oxidized to form a disulfide bond (Freedman, Curr. Op. Struct. Biol. (1995) 5, 85-91; Creighton et al., TIBTECH 1995 (13), 18-23; Raina, Annu. Rev. Microbiol. (1997) 51, 179-202. The rate of disulfide-bond formation depends on the proximity of the two cysteine residues, defined as the probability of their sulfur atoms coming within the distance required for thiol/disulfide exchange. Disulfide bonds, which are also termed disulfide bridges (synonyms are SS bonds and SS bridges, respectively), constitute covalent tertiary contacts and usually contribute to the stabilization of the folded conformation. They do so by restricting the conformational flexibility of an unfolded polypeptide chain, i.e. the contribution of SS bonds to the stability of a protein is rather entropic than enthalpic in nature. The formation of disulfide bonds requires an oxidative environment. Therefore, intracellular proteins barely contain disulfide bridges because intracellular compartments, such as the bacterial cytoplasm or the eucaryotic cytosol, are essentially reductive. However, disulfide bridges occur frequently in secreted or translocated proteins, such as the gp41 and gp36 ectodomains from HIV-1 and HIV-2, respectively, and in the rubella envelope proteins E1 and E2.

Surprisingly, it has been found that a soluble rubella E1 antigen variant is obtained by deletion of the transmembrane region and the C-terminal anchor segment, preferably from amino acid residues 453-481. Most preferably in addition the α-helical region from amino acids 453 to about 468 is also deleted. Within the N-terminal region at least the amino acid residues 143-164, more preferable from amino acid 134 to about 168 must also be deleted.

Combination of the disulfide bridges Cys 8-Cys 13, Cys 59-Cys 71, Cys 117-Cys 130 and the disulfide bridges Cys 176-Cys 185, Cys 225-Cys 235, Cys 349-Cys 352 and Cys 368-Cys 401, respectively, when the transmembrane region and the C-terminal anchor segment as well as at least the amino acids 143-164, preferably 134 to about 168 are lacking, yields the most extended rubella E1 antigen according to the present invention which is still soluble and contains as many epitopes as possible with a preferable high immunological reactivity in a serological assay.

The N-terminal region within the rubella E1 envelope protein and variants thereof according to the present invention contains preferably at least the region comprising the disulfide bridges Cys 8-Cys 13 and Cys 59-Cys 71, more preferably the disulfide bridge combination Cys 8-Cys 13 and Cys 59-Cys 71 and Cys 117-Cys 130. The combination of the disulfide bridges Cys 8-Cys 13 and Cys 59-Cys 71 and Cys 117-Cys 130 has an beneficial effect on the rubella E1 fragment according to the present invention because it ensures the tertiary fixing of certain rubella E1 epitopes with a high immunological reactivity antigen.

The C-terminal region within the rubella E1 antigen and variants thereof according to the present invention contains at least the region comprising the disulfide bridges Cys 349-Cys 352 and Cys 368-Cys 401, more preferably the combination of the disulfide bridges Cys 225-Cys 235, Cys 349-Cys 352 and Cys 368-Cys 401 or the combination of the disulfide bridges Cys 176-Cys 185, Cys 349-Cys 352 and Cys 368-Cys 401, most preferably the combination of the disulfide bridges Cys 176-Cys 185, Cys 225-Cys 235, Cys 349-Cys 352 and Cys 368-Cys 401. The combination of the disulfide bridges Cys 225-Cys 235, Cys 349-Cys 352 and Cys 368-Cys 401 or the combination of the disulfide bridges Cys 176-Cys 185, Cys 349-Cys 352 and Cys 368-Cys 401 has an additional effect on the rubella E1 antigen because it allows the accessibility of main epitopes with a high immunological reactivity.

For determination of the main immunoreactivity of the rubella E1 antigen the protein was firstly divided for our purpose into a N-terminal part comprising the amino acids residues 1-314 and into a C-terminal part comprising amino acid residues 315-432. The sequences of both parts were designed without cysteines to prevent refolding artifacts due to disulfide shuffling and were further cloned into expression vectors.

Afterwards, each single disulfide-bridge of the rubella E1 peptide as described in Gros et al., (1997) was inserted into the N-terminal and C-terminal part individually and in combination. The importance of the covalent tertiary contacts for epitope fixing was assessed by means of the respective immunological reactivity.

Interestingly, it is obvious from gel-filtration analysis that the N-terminal fragment (1-314) appears as a high-molecular associate, whereas the C-terminal fragment (315-432) apparently elutes as a dimer. This is in contrast to the-state-of-the-art described in Baron and Forsell, (1991), disclosing rubella E1/E2 peptides as a conglomerate consisting of monomers, homo-and hetero-dimers. The results of the present invention further revealed that the different solubility characteristics correlate with the expression activity: while the production rate of the N-terminal segment (1-314) was only around 1 mg protein/g biomass, the production rate of the C-terminal segment (315-432) strikingly exceeded 20 mg protein/g wet cell weight.

The cysteine-free variants displayed no significant immunological reactivity when assessed with rubella-positive sera in an automated ELECSYS analyzer. Importantly, single disulfide bridges or the combination of disulfide bridges within the N-terminal fragment (1-314) showed no significant increase in reactivity. However, the reactivity of the C-terminal fragment (amino acid residues 315-432) was significantly increased by inserting the disulfide bridges Cys 349-Cys 352, and Cys 368-Cys 401. The reason for the missing reactivity of the N-terminal rubella E1 protein could be due to a structure element within the sequence mediating aggregation or association and thus compromising accessibility of the main epitopes.

To further prove this assumption the N-terminal fragment (amino acid residues 1-314) of the rubella E1 envelope protein was stepwise truncated from its C-terminal end. Likewise, the C-terminal fragment (315-432) was gradually extended at its N-terminal end. It was expected that the C-terminal fragment would get insoluble at a certain degree of extension, whereas the N-terminal fragment would be rendered soluble at a certain degree of truncation.

For expression and characterization the C-terminal variants E1-C(aa 260-432), E1-C(aa 201-432), E1-C(aa 143-432), E1(aa 105-432), E1(aa 56-432) and E1(aa 34-432) were used. The variants E1(aa 201-432), E1(aa 260-432), and E1(aa 315-432) form stable dimers, whereas the longer constructs are extremely prone to aggregation and association. Thus the oligomerisation motif of the E1 ectodomain was confined to a region around 143 aa to about 200 aa. For a more precise mapping the fragment E1 (169-432) was cloned, expressed and characterized. Surprisingly, this construct formed both stable and soluble dimers and was therefore a good candidate for the detection of anti-rubella IgG molecules. On the basis of this result the association motif could be confined to the segment 143 aa to 168 aa. For a more detailed mapping the fragments E1 (156-432) and E1 (163-432) were characterized. Both constructs elute partially as dimers, partially as aggregates of high molecular weight and were therefore of limited value as antigens for the detection of anti-rubella IgG antibodies in a one-step double antigen sandwich format.

As a main result of this test series of the present invention it could be clearly shown, that it is possible to extend the C-terminal E1 (315-432) fragment from amino acid residue 315 until amino acid residue 169 without compromising the solubility, the oligomerisation state, and the stability.

Secondly, the region between the first and the second third of the E1 ectodomain (143-168) contains a structure- or sequence motif, which is responsible for the association of the protein to form high-molecular-weight-aggregates. The immanent hydrophobicity of this region is puzzling because it can not be deduced from a simple primary structure analysis. The region comprising the association motif markedly restricts the use of the E1 envelope protein for the serological detection of IgG molecules.

A comparable procedure was used for the optimization of the solubility of the N-terminal segment. The E1 fragments E1-N (1-200), E1-N (1-142), E1-N (1-104) and E1-N (1-55) were cloned into expression vectors, transferred into *E. coli* host cells, expressed and characterized. As expected, the longest N-fragment (ectodomain 1-200) elutes as a high molecular-weight aggregate and thus strongly resembles the E1 ectodomain variant E1-N (1-314). Significantly improved solubility properties were achieved with the truncated fragment E1-N (1-142) eluting partially as a soluble dimer, partially as a high molecular-weight aggregate. Finally, the truncated variants E1-N (1-104) and E1-N (1-55) apparently eluted as dimers. The region between amino acid residues 104 and 142 was further analysed by use of fragments E1-N-(1-117) and (1-133). Both variants appeared as soluble dimers in FPLC-analysis and thus fulfill an important prerequisite for the serological detection of IgG-molecules. However, the variant E1-N (1-117) was more stable and therefore the better candidate for further optimization experiments.

Briefly, two regions of the rubella E1 protein were identified after length-optimization in the present invention, which are very well expressed in *E. coli* and which form soluble dimers: The N-terminal fragment (E1-N) comprising the amino acid residues 1-117/1-133, and the C-terminal fragment (E1-C) comprising the region 169-432/201-432. By means of these E1 fragments the question which disulfide bridges were important for the antigenicity of the recombinant rubella E1 ectodomain was addressed. Therefore, the cystein-pairs were reconstituted-individually and in combination-and the corresponding E1 variants were assessed in an automated ELECSYS 2010 analyser (Roche Diagnostics GmbH) with anti-rubella positive sera.

The following cysteine-variants were characterized in rubella E1 (201-432): the single-bridge variants Cys 225-Cys 235, Cys 349-Cys 352 and Cys 368-Cys 401, the double-bridge-combination Cys 349-Cys 352/Cys 368-Cys 401 and the triple-bridge-combination Cys 225-Cys 235/Cys 349-Cys 352/Cys 368-Cys 401. Furthermore, the double-combination Cys 176-185/Cys 225-Cys235 was analysed in the extended construct E1 (169-432).

The following cysteine combinations were characterized in the rubella E1 fragment 1-133: the single-bridge variants Cys 8-Cys13, Cys 59-Cys71and Cys 117-Cys 130 and the double-bridge-combinations Cys 8-Cys13/Cys59-Cys71, Cys8-Cys13/Cys 117-130 and Cys 59-Cys 71/Cys 117-Cys 130. Moreover, the double-bridge-combination Cys 8-Cys 13/Cys 59-Cys 71 was characterized in fusion construct E1-N (1-117) and E1-N (1-104). Immunological assessment of the rubella E1 variants in an automated ELECSYS 2010 analyser revealed that the antigenicity depends on the native-like conformation of the ectodomain molecule, which is fixed by the covalent tertiary contacts mediated by the disulfide bridges.

Surprisingly, these diagnostics findings demonstrate that in terms of immunoreactivity different emphasis has to be placed on the disulfide bridges of the rubella E1 antigen. The disulfide bridges Cys-349-Cys-352 as well as Cys-368-Cys-401 play a decisive role. The increase in sensitivity by combination of these disulfide bridges was interestingly not additive, but cooperative. The assessment of construct E1-C (201-432) demonstrates significant signals for the tertiary fixation of Cys 349-Cys 352 as well as for Cys 368-Cys 401 in each case. By combination of both bridges the level of signal surprisingly increased at a multiple compared to the single-bridge-constructs. Presumably, a native-like conformation of the rubella E1 ectodomain is fixed through the two intramolecular combinations, detecting a higher quantity of specific IgG-molecules in rubella positive sera. The relevance of the covalent tertiary contacts is particularly apparent by the immunological evaluation of the cystein-free construct E1-C (201-432). Surprisingly, no positive signals are measurable the cystein-free construct in contrast to the single-bridge-constructs.

The immunological detection of anti-rubella IgG antibodies in native samples was further improved with the optimized antigen E1-C (201-432, Cys 349-Cys352, Cys 368-Cys 401). All human sera applied in these studies which were classified as anti-rubella IgG positive, were found positive. By using the more complex tertiary-bridges fusion construct -E1-C(169-432), Cys 225-Cys 235, Cys 349-Cys352, Cys 368-Cys 401) equivalent results could be obtained for the detection of anti-rubella IgG antibodies.

The minimal requirement for a rubella E1 antigen-fragment could be reduced to a polypeptide backbone intramolecularly connected at least by the disulfide bridges Cys 349-Cys 352 and Cys 368-Cys 401. As the E1 fragment E1-C (342-412, Cys 349-Cys 352, Cys 368-Cys 401) exhibits insufficient immunological reactivity, sequence-elements adjacent to the N-terminus and/or C-terminus of E1-C (342-412) were considered to be important for the immunological reactivity. To demonstrate this, the construct E1-C (315-412, Cys 349-Cys 352, Cys 368-Cys 401) was cloned and characterized. For this fragment immunological reactivity could be shown which was comparable to E1-C(201-432, Cys 349-Cys 352, Cys 368-Cys 401). This result demonstrates that the amino acid residues of N-terminal region (315-342) of construct E1-C (amino acid 315-412) seems to be important for the immunological reactivity of the rubella E1 antigen. An average man skilled in the art is able to proof by further experiments which sequence elements adjacent to the N-terminus and/or C-terminus of E1-C (315-412) are important for the immunological reactivity.

In addition to the high-reactive fragment with disulfide bridges from the C-terminal part of the ectodomain, several N-terminal fragments were cloned and expressed. They revealed significant immunological reactivity. Immunoreactivity was obtain from the two double-bridge fusion constructs E1-N (1-117, Cys 8- Cys13/Cys 59-Cys 71) and E1-N (1-133, Cys 8- Cys13/Cys 59-Cys 71).

The longest rubella E1 fragment which can be refolded into a soluble and immunoreactive conformation spans from amino acid residues 1-133 comprising the disulfide bridges Cys 8-Cys 13 and Cys 59-Cys 71, more preferable the disulfide bridges Cys 8-Cys 13 and Cys 59-Cys 71 and Cys 117-Cys 130 and from amino acid residues 169-432 comprising the disulfide bridges Cys 349-Cys 352 and Cys 368-Cys 401 and the combination of the disulfide bridges Cys 225-Cys 235, Cys 349-Cys 352 and Cys 368-Cys 401 or the combination of the disulfide bridges Cys 176-Cys 185, Cys 349-Cys 352 and Cys 368-Cys 401, most preferable the combination of the disulfide bridges Cys 176-Cys 185, Cys 225-Cys 235, Cys 349-Cys 352 and Cys 368-Cys 401 by lacking at the C-terminal end at least the transmembrane region and the short C-terminal anchor segment as well as at least the amino acids 143-164, preferably the amino acids 134-168.

A preferred embodiment of the present invention is therefore a soluble rubella E1 antigen and variants of this peptide containing the region spanning the disulfide bridges Cys 349-Cys 352 and Cys 368-Cys 401 and additional at least the region spanning the disulfide bridges Cys 225-Cys 235.

A further subject matter of the present invention relates to a soluble rubella E1 antigen and variants of this peptide containing the region spanning the disulfide bridges bridges Cys 225-Cys 235, Cys 349-Cys 352 and Cys 368-Cys 401 and additional at least the region spanning the disulfide bridges Cys 176-Cys 185. Furthermore, the combination of the disulfide bridges Cys 349-Cys 352 and Cys 368-Cys 401, more preferable the combination of the disulfide bridges bridges Cys 225-Cys 235, Cys 349-Cys 352 and Cys 368-Cys 401 or the combination of the disulfide bridges Cys 176-Cys 185, Cys 349-Cys 352 and Cys 368-Cys 401, most preferable the combination of the disulfide bridges Cys 176-Cys 185, Cys 225-Cys 235, Cys 349-Cys 352 and Cys 368-Cys 401 is a preferred embodiment of the present invention. These rubella E1 antigens contain the main immunological reactivity for the formation of epitopes.

A further preferred embodiment of the present invention relates to a soluble rubella E1 antigen and variants of this protein in addition containing, to the disulfide bridges Cys 176-Cys 185, Cys 225-Cys 235, Cys 349-Cys 352 and Cys 368-Cys 401, the region spanning the disulfide bridges bridges Cys 8-Cys 13 and Cys 59-Cys 71, more preferable the disulfide bridges Cys 8-Cys 13 and Cys 59-Cys 71 and Cys 117-Cys 130.

The region of the rubella E1 antigen, spanning at least the disulfide bridges bridges Cys 8-Cys 13 and Cys 59-Cys 71, more preferable the disulfide bridges Cys 8-Cys 13 and Cys 59-Cys 71 and Cys 117-Cys 130 contain as well certain immunological reactivity for the formation of epitopes. It is also possible to use these N-terminal fragments without being linked to the C-terminal sequences containing the disulfide bridges Cys 176-Cys 185, Cys 225-Cys 235, Cys 349-Cys 352 and Cys 368-Cys 401. Preferably these N-terminal rubella E1 antigens will be used in an assay in combination with the C-terminal rubella E1 antigens as described above.

In the present invention comprehensive regions and fragments of the rubella E1 ectodomain were identified which were recombinantly expressed in *E. coli* and which were in vitro reproducible refolded into a functional conformation. The E1 fragments of the present invention optimized in regard to their length and their yield of cysteins are soluble and are in particular suitable for the detection of anti-rubella IgG in rubella-positive sera.

This finding is in contrast to the known rubella E1 fragments (Newcombe et al., (1994), Starkey et al., (1995), EP0299673). These known constructs do not contain the combination of the disulfide bridges Cys 349-Cys 352 and Cys 368-Cys 401 and therefore they miss the main immunological reactivity for the formation of epitopes. Furthermore, the known constructs do not disclose the disulfide bridges of the N-terminal region Cys 8-Cys 13 and Cys 59-Cys 71 and Cys 117-Cys 130 and/or the combination of the disulfide bridges of the C-terminal region and the N-terminal region by lacking at the C-terminal end at least the transmembran region as well as at least the amino acids 143 to 164, preferably the amino acids 134 to about 168 as disclosed in the present invention which can be refolded into a highly soluble and immunoreactive conformation. Furthermore, preferred fusion constructs of the present invention may contain longer parts of rubella E1 protein with more epitopes because they are soluble and are therefore more suitable for the detection of most of the anti-rubella antibodies.

The term "variants" refers to sections of sequences of different length of the rubella E1 ectodomain, which may comprise a different amount of cysteine-pairs. These sequences, the nucleic acid sequence of the inserted cassette and the amino acid sequence of the resulting fusion polypeptide of the rubella E1, are described in the sequence protocol of the present invention.

Furthermore, the term "variants" in this context relates to protein substantially similar to said protein. In particular, a variant may be an isoform or allele which shows amino acid exchanges, deletion or insertions compared to the amino acid sequence of the most prevalent protein isoform. Preferable, such a substantially similar protein has a sequence similarity to the most prevalent isoform of the protein of at least 80%, preferable at least 85%, more preferable at least 90%, most preferably at least 95%.

The term "variant" also relates to a post-translationally modifed protein such as glycosylated protein. A "variant" is also a protein which has been modified after collection of the sample, for example by covalent or non-covalent attachment of a label, particularly a radioactive fluorescent label, to the protein. Other possible labels are radioactive, fluorescent, chemiluminescent, electrochemiluminescent, enzymes or others. Further "variants" are solid phase binding groups like e.g. biotinylated proteins, a detailed description of labels is disclosed on page 24 and 25 of the present invention.

The rubella E1 antigen can be produced by chemical synthesis, the synthesis can be carried out in homogeneous solution or in solid phase. For instance, the synthesis technique in homogeneous solution, which can be used, is the one described by Houbenweyl in "Methode der Organischen Chemie" edited by E. Wunsch, vol 15-I et II, Thiem, Stuttgart, Germany, 1974. The protein of the invention can also be prepared in solid phase according to the methods described by Artherton and Shepard in "Solid phase peptide synthesis" IRL Press, Oxford, UK, 1989.

The above described rubella E1 proteins optimized for solubility and a defined monomeric or oligomeric state also offer the potential for IgM detection-modules. For this purpose, the E1 fusion proteins which are apparent as dimers might be polymerized, e.g. by chemical cross-linking. A further preferred embodiment of the present invention is a mixed polymer composed of protein E1, E2 and Core protein C. Rubella E2 and Core proteins are known in the art.

The rubella E1 protein according to this invention can also be prepared by means of recombinant DNA techniques. The term "recombinant DNA molecule" refers to a molecule which is made by the combination of two otherwise separated segments of sequence accomplished by the artificial manipulation of isolated segments of polynucleotides by genetic engineering techniques or by chemical synthesis. In doing so one may join together polynucleotide segments of desired functions to generate a desired combination of functions.

Large amounts of the polynucleotides may be produced by replication in a suitable host cell. Natural or synthetic DNA fragments coding for proteins or fragments thereof will be incorporated into recombinant polynucleotide constructs, typically DNA constructs, capable of introduction into and replication in a prokaryotic or lower or higher eukaryotic cell such as described by Sambrook, J., et al. Molecular Cloning: a Laboratory Manual, 2nd ed., Cold Spring Harbor Press, NY, (1989). The term "lower eukaryotes" refers to host cells such as yeast, fungi and the like. Lower eukaryotes are generally (but not necessarily) unicellular. The term "prokaryotes" refers to hosts such as *E. Coli, Lactobacillus, Lactococcus, Salmonella, Streptococcus, Bacillus subtillis* or *Streptomyces*. Also these hosts are contemplated within the present invention. Preferred lower eukaryotes are yeast's, particularly species within *Schizosaccharomyces, Saccharomyces, Kluiveromyces, Pichia* (e.g. *Pichia pastoris*), *Hansenula* (e.g. *Hansenula polymorpha*), *Schwaniomyces, Schizosaccharomyces, Yarowia, Zygosaccharomyces* and the like. *Saccharomyces cerevisiae, S. carlsbergensis* and *K. lactis* are the most commonly used yeast hosts, and are convenient fungal hosts. The term "higher eucaryotes" refers to host cells derived from animals, such as mammals, reptiles, insects, and the like. Presently preferred higher eukaryote host cells are derived from Chinese hamster (e.g. CHO), monkey (e.g. COS and Vero cells), baby hamster kidney cells (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like.

In a preferred embodiment according to the invention, the rubella E1 antigen is produced as a recombinant fusion protein. The term "fusion protein" as used in the present invention, refers to a protein comprising at least one protein domain corresponding to a rubella E1 protein and at least one protein domain corresponding to another fusion protein, preferably to the FKBP (FK binding protein) chaperone used as expression tool as described below.

Other extensively used fusion proteins are e.g. the glutathione S-transferase (GST) fusion protein system for high level expression and rapid purification of fusion proteins from bacterial and eukaryotic cell lysates.

Folding and purification of proteins is often facilitated by fusing them covalently with tags or partner proteins that fold robustly by themselves. These fusion modules include maltose binding protein, glutathion S-Transferase, thioredoxin, NusA, DsbA and FkpA. Their use customarily aims at increasing the soluble expression (i.e. the native-like folding) of the respective target protein either in the cytosol or the periplasm of the overproducing E. coli host. Chaperones play an increasingly important role in the biotechnological production of soluble and functional proteins. Preferably chaperones are used as fusion proteins within the rubella E1 fusion polypeptide.

Chaperones, which are known as classical "folding helpers", are proteins that assist the folding and maintenance of structural integrity of other proteins. They possess the ability to promote the folding of a protein both in vivo and in vitro. Generally, folding helpers are subdivided into folding catalysts and chaperones. Folding catalysts accelerate the rate limiting steps in protein folding due to their catalytic function. Chaperones are known to bind to denatured or partially denatured proteins and thus help to re-nature proteins. Thus, unlike folding catalysts, chaperones exert a mere binding function (Buchner, J., Faseb J 10 (1996) 10-19). Examples of catalysts and chaperones are described in detail in WO 03/000877.

To date, several different families of chaperones are known. All these chaperones are characterized by their ability to bind unfolded or partially unfolded proteins and have a physiological function that is linked to the correct folding of proteins or the removal of denatured or aggregated protein. Further, it has been demonstrated in WO 94/08012 that an enhanced expression of chaperones may facilitate the recombinant production of a protein. It is also known that an increased production of proteins can be achieved by using a gene construct comprising a protein coding sequence as well as a chaperone sequence. The approach to use chaperones for increased production of native-like folded protein is mainly due to the binding and thus solubilizing function of chaperone proteins. After recombinant production of a fusion protein comprising chaperone and target protein, the chaperones are customarily cleaved off from the resulting protein to yield the desired protein in pure form.

It has been demonstrated in WO 03/000877 that folding helpers, e.g., many members of the peptidyl prolyl isomerase (PPI) class, especially from the FKBP family, not only exhibit catalytic activity, but also bring about drastic beneficial effects on solubility of proteins tending to aggregation. They do so by forming soluble complexes with such proteins that are otherwise (i.e. in an unchaperoned, isolated form) prone to aggregation. Such proteins that are otherwise hardly soluble or insoluble under physiological conditions turn out to be soluble under mild physiological conditions (i.e. without need for solubilizing additives such as detergents or chaotropic agents) once they are bound in a complex with the appropriate PPI chaperone.

We found that the recombinantly produced fusion protein according to the present invention can be readily obtained from inclusion bodies in soluble form. A striking feature of rubella E1 protein comprised in a recombinantly produced rubella E1 protein is its solubility at physiological buffer conditions. Moreover, the rubella E1 protein according to the present invention comprised in a fusion protein readily can be obtained in a native-like structure.

The rubella E1 fusion protein according to the present invention also is very easy to handle, e.g., it is quite easy to renature such fusion protein. It is interesting that the chaotropic material can be refolded in different ways, all resulting in a thermodynamically stable and soluble native-like form. Refolding is achieved at high yields, both by dialysis and by rapid dilution, as well as by renaturing size exclusion chromatography or matrix-assisted refolding. These findings suggest that in this covalently linked form, the rubella E1 antigen fusion protein is a thermodynamically stable rather than a metastable protein.

Preferably, a soluble protein according to the present invention can be produced by fusion of a rubella E1 antigen with a peptidyl-prolyl-isomerase class chaperone. Therefore, a preferred embodiment according to the invention relates to the fusion of a rubella E1 antigen with a peptidyl-prolyl-isomerase class chaperone.

A further subject matter of the present invention relates a recombinant DNA molecule, encoding a rubella E1 antigen, comprising at least one nucleotide sequence coding for a rubella E1 antigen wherein upstream thereto is at least one nucleotide sequence coding for a FKBP chaperone.

Prolyl isomerases may comprise different subunits or modules of different function, e.g., a module exhibiting catalytic activity and a module exhibiting the chaperone or binding activity. Such modular members of the FKBP family are FkpA (Ramm, K. and Pluckthun, A., J Biol Chem 275 (2000) 17106-13), SlyD (Hottenrott, S., et al., J Biol Chem 272 (1997) 15697-701) and trigger factor (Scholz, C., et al., Embo J 16 (1997) 54-8). In a preferred embodiment the invention relates to a recombinant DNA molecule, characterized in that the FKBP chaperone is selected from the group consisting of FkpA, SlyD, and trigger factor.

It is also well known and appreciated that it is not necessary to always use the complete sequence of a molecular chaperone. Functional fragments of chaperones (so-called modules) which still possess the required abilities and functions may also be used (cf. WO 98/13496).

The FkpA used as expression tool according to the present invention lacks the N-terminal signal sequence. A close relative of FkpA, namely SlyD, consists of a structured N-terminal domain responsible for catalytic and chaperone functions and of a largely unstructured C-terminus that is exceptionally rich in histidine and cysteine residues (Hottenrott, S., et al., J Biol Chem 272 (1997) 15697-701). WO 03/000878 discloses that a C-terminally truncated variant of SlyD comprising amino acids 1-165 exerts exceptionally positive effects on the efficient expression of target proteins. Unlike in the wild-type SlyD, the danger of compromising disulfide shuffling is successfully circumvented in the truncated SlyD-variant (1-165) used. A recombinant DNA molecule comprising a truncated SlyD (1-165) represents a preferred embodiment of the present invention.

In a preferred mode of designing a rubella E1 antigen according to the present invention, no signal peptides are included. The expression systems according to the present invention have been found most advantageous when working as cytosolic expression system. This cytosolic expression results in the formation of inclusion bodies. Different from the pronounced and well-known problems usually associated with inclusion bodies, we now have found that not only an exceptionally high amount of rubella E1 protein is produced, but that the recombinant rubella E1 protein according to the present invention are also easy to handle, e.g. easy to solubilize and to refold.

Preferably the recombinant DNA molecule of the present invention is further characterized in that it comprises at least one nucleotide sequence coding for a peptidic linker of 10-100 amino acids located in between said sequence coding for a rubella E1 antigen and said sequence coding for the FKBP chaperone. As the skilled artisan will appreciate such linker polypeptide is designed as most appropriate for the intended application, especially in terms of length, flexibility, charge, and hydrophilicity. Furthermore, such DNA sequence coding for a linker in addition to e.g., provide for a proteolytic cleavage site, may also serve as a polylinker, i.e., it may provide multiple DNA restriction sites to facilitate fusion of the DNA fragments coding for a rubella E1 protein and a chaperone domain. After expression and purification of the obtained fusion protein and further refolding into a soluble and immunoreactive conformation the polylinker facilitates as well the release of the rubella E1 protein out of the fusion protein complex.

Thereby, a soluble rubella E1 antigen and variants of this protein according to the present invention can be excised out of the fusion construct wherein the rubella E1 antigen is characterized by lacking at the C-terminal end at least the transmembran region and the anchor segment as well as at least the amino acids 143 to 164 and containing at least the region spanning the disulfide bridges Cys 349-Cys 352 and Cys 368-401 whereas the N-terminus (Cys 349) of this region contains additionally at least 15 amino acids and/or the C-terminus (Cys 401) of this region contains additionally at least 8 amino acids of the adjacent rubella E1 antigen sequence. Furthermore, the N-terminus (Cys 349) of the above described region of the rubella E1 antigen contains additionally at least 25, 30, 34 amino acids and/or the C-terminus (Cys 401) of this region contains additionally at least 10, 11, 15, 25, 35 amino acids of the adjacent rubella E1 antigen sequence.

A further subject matter of the invention relates to a recombinant DNA which comprises a single nucleotide sequence coding for a FKBP chaperone and a single nucleotide sequence coding for a rubella E1 protein.

A fusion protein comprising at least two FKBP chaperone domains and one target protein domain is also very advantageous. In a further preferred embodiment the recombinant DNA molecule according to the present invention comprises two sequences coding for a FKBP chaperone and one sequence coding for a rubella E1 protein. Scholz et al., (2005) demonstrate that the solubility of a fusion protein is markedly improved when a second chaperone unit is fused. There is evidence to suggest that the naturally dimeric PPIase is closely mimicked by fusion of two FKPB-chaperone domains which results in the improved solubility.

As the skilled artisan will appreciate the term "at least two" is used to indicate that two or more nucleotide sequences coding for a FKBP chaperone domain may be used in construction of a recombinant DNA molecule without departing from the scope of the present invention. Preferably, the rubella E1 chaperone protein will contain at least two and at most four sequences coding for a chaperone.

The DNA molecule may be designed to comprise both the DNA sequences coding for the FKBP chaperone upstream to the target protein. Alternatively the two FKBP-domains may be arranged to sandwich the target protein. A recombinant DNA molecule comprising both FKBP-domains upstream to the sequence coding for a rubella E1 antigen represents a preferred embodiment according to the present invention.

In an alternative embodiment of the invention the recombinant DNA molecule is characterized in that one sequence coding for a PPI chaperone is located upstream of a rubella E1 antigen and the other sequence coding for a PPI chaperone is located downstream of the sequence coding for a rubella E1 antigen.

The DNA construct comprising two chaperone domains as well as a sequence coding for a rubella E1 antigen preferably also contains two linker peptides of 10 to 100 amino acids in between these domains. In order to allow for a systematic cloning the nucleotide sequences coding for these two linker peptide sequences preferably are different. This difference in nucleotide sequence must not necessarily result in a difference in the amino-acid sequence of the linker peptides. In yet a further preferred embodiment the amino acid sequences of the two linker peptides are identical. Such identical linker peptide sequences for example are advantageous if the fusion protein comprising two FKBP chaperone domains as well as the rubella E1 protein is to be used in an immunoassay.

In cases where it is desired to release one or all of the chaperones out of a fusion protein according to the present invention the linker peptide is constructed to comprise a proteolytic cleavage site. As previous described the proteolytic cleavage site may also serve as a polylinker, i.e., it may provide multiple DNA restriction sites to facilitate fusion of the DNA fragments coding for a rubella E1 protein and a chaperone domain. A recombinant DNA molecule encoding a fusion protein comprising at least one polypeptide sequence coding for a rubella E1 protein, upstream thereto at least one nucleotide sequence coding for a FKBP chaperone selected from the group consisting of FkpA, SlyD, and trigger factor and additionally comprising a nucleic acid sequence coding for a peptidic linker comprising a proteolytic cleavage site, represents a further embodiment of this invention.

An expression vector comprising operably linked a recombinant DNA molecule according to the present invention, i.e., a recombinant DNA molecule encoding a fusion protein comprising at least one polynucleotide sequence coding for a rubella E1 protein and upstream thereto at least one nucleotide sequence coding for a FKBP chaperone, wherein the FKBP chaperone is selected from FkpA, SlyD, and trigger factor, has proven to be very advantageous.

The expression vector comprising a recombinant DNA according to the present invention may be used to express the fusion protein in a cell free translation system or may be used to transform a host cell. In a preferred embodiment the present invention relates to a host cell transformed with an expression vector according to the present invention.

Expression and cloning vectors will likely contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g. ampicillin, tetracycline, etc.; (b) complement auxotrophic deficiencies; or (c) supply critical nutrients not available from complex media. The choice of the proper selectable marker will depend on the host cell, and appropriate markers for different hosts are known in the art.

The vectors containing the rubella E1 protein of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses. Large quantities of the rubella E1 protein of the present invention may be prepared by expressing the polypeptides of the present invention in vectors or other expression vehicles in compatible host cells.

Construction of a vector according to the present invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labeled probe which may be based on a sequence provided herein. Those skilled in the art will readily envisage how these methods may be modified, if desired.

A further preferred embodiment of the present invention comprises a method of producing a soluble and immunoreactive rubella E1 antigen-chaperone fusion protein, said method comprising the steps of culturing host cells, expressing said fusion protein, purifying said fusion protein, and refolding the fusion protein into a soluble and immunoreactive conformation.

The method according to the invention relates to the production of a soluble and immunoreactive rubella E1 antigen-chaperone fusion protein, wherein the peptidyl prolyl isomerase is a FKBP chaperone. Furthermore, said method relates to a FKBP chaperone which is selected from the group consisting of SlyD, FkpA, and trigger factor.

A further subject matter of the present invention is a method for the detection, determination and quantification of anti-rubella antibodies of the subclasses IgG and/or IgM in a sample wherein the rubella E1 antigen is used as a capture reagent and/or binding partner for the antibodies. All biological liquids known to the expert can be used as samples for the detection of anti-rubella antibodies. The samples preferred are body liquids like whole blood, blood sera, blood plasma, urine, saliva, etc.

With respect to diagnostic procedures, obvious advantages of a soluble rubella E1 antigen fusion protein, more preferable a soluble rubella E1 antigen-chaperone protein according to the present invention are, e.g., the increased stability of the rubella E1 protein under physiological buffer conditions, the increase in diagnostic sensitivity, the increased numbers of conformational epitopes present, and the possibility to easily label a correctly folded rubella E1 protein.

Well-known labels are marker groups or effector groups, like solid phase binding groups. A labeled soluble rubella E1 antigen fusion protein, more preferable a labeled soluble rubella E1 antigen-chaperone protein represents a further preferred embodiment according to the present invention.

The labeling group can be selected from any known detectable marker groups, such as dyes, luminescent labeling groups such as chemiluminescent groups, e.g., acridinium esters or dioxetanes, or fluorescent dyes, e.g., fluorescein, coumarin, rhodamine, oxazine, resorufin, cyanine and derivatives thereof. Other examples of labeling groups are luminescent metal complexes, such as ruthenium or europium complexes, enzymes, e.g., as used for ELISA or for CEDIA (Cloned Enzyme Donor Immunoassay, e.g., EP A 61,888), and radioisotopes.

Effector groups comprise, for example, one partner of a bioaffinity binding pair. While performing an assay, the effector group interacts specifically and preferably non-covalently with the other partner of the bioaffinity binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred binding pair members comprise hapten, antigen and hormone. Especially preferred are haptens like digoxin and biotin and analogues thereof.

Preferable, the soluble complex comprising a rubella E1 protein and preferable a PPI chaperone is used in an immunoassay for detection of antibodies to rubella. In a further preferred embodiment, a labeled soluble complex comprising a rubella E1 antigen and a preferable PPI chaperone is used in an immunoassay for detection of antibodies to rubella. Most preferred, the labeled complex is an intramolecular complex within a recombinant polypeptide comprising preferable the PPI chaperone and a rubella E1 protein.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates in "Practice and theory of enzyme immunoassays" (1990) 221-278, Eds. R. H. Burdon and v. P. H. Knippenberg, Elsevier, Amsterdam) and various volumes of Tijssen, in "Methods in Enzymology" (1980), Eds. S. P. Colowick, N. O. Caplan and S. P., Academic Press), dealing with immunological detection methods, especially volumes 70, 73, 74, 84, 92 and 121.

The novel soluble rubella E1 antigen fusion protein, more preferable the novel soluble rubella E1 antigen-PPI chaperone protein can be used to improve assays for the detection of anti-rubella antibodies independently of the mode of detection (e.g., radioisotope assay, enzyme immunoassay, electrochemiluminescence assay, etc.) or the assay principle (e.g., test strip assay, sandwich assay, or homogenous assay, etc.).

For the reliable and sensitive early detection of a rubella infection, it is essential to measure anti-viral antibody in bodily fluid samples. The soluble complex according to the present invention enables the detection of anti-rubella antibodies at physiological buffer conditions. The detection of anti-rubella antibodies is a valuable part of such combined rubella detection systems. In a preferred embodiment, the present invention therefore relates to rubella detection systems comprising the detection of anti-rubella antibodies based on the use of a rubella E1 antigen fusion protein, more preferable the use of a rubella E1 antigen- chaperone protein.

As known from the art, antibodies to infectious agents such as bacteria, fungi or viruses, are preferably detected by an assay performed according to the double antigen bridge concept (sometimes this assay concept is also termed double antigen bridge concept, because the two antigens are bridged by an antibody). In such an assay the ability of an antibody to bind at least two different molecules of a given antigen with its two (IgG, IgA, IgE) or 10 (IgM) paratopes is required and used.

Detection of antibodies from bodily fluids according to the bridge concept can be performed in many different assay setups. A simple setup comprises the direct coating of an antigen to a solid phase and the use of the same antigen in a labeled form. Under appropriate assay conditions, an antibody in a sample forms a bridge between the solid phase bound antigen and the labeled antigen. Therefore, only if the antibody under investigation is present in the sample is a bridge formed, and a signal can be detected.

The basic structures of "solid phase antigen" and the "detection antigen" preferably are the same. For example, a protein comprising one or several epitopes may be used directly or indirectly coated to a solid phase, and the same synthetic protein, however, bound to a label or marker is used as detection antigen. It is also possible to use similar but different rubella E1 antigens, which are immunologically cross-reactive in a double antigen bridge assay. The essential requirement for performing such assays is that the relevant epitope or the relevant epitopes are present on both antigens. Obviously, there are many variants of the double antigen bridge assay format. Such variants comprise, for example, the indirect coating of a rubella E1 antigen to a solid phase. Preferably, a specific binding pair, most preferably the biotin-streptavidin (or-avidin) system, is used to indirectly bind a rubella antigen to a solid phase. On the other hand, the rubella E1 antigen used for detection in such a system may not directly carry a marker (e.g., a radioisotope, enzyme, fluorescent molecule, etc.), but rather may be indirectly detectable by, e.g., carrying a hapten (for example, digoxin). Such indirect detection then, e.g., may be performed by a labeled anti-digoxin antibody.

A preferred embodiment of the present invention is therefore an immunoassay according to the double antigen bridge concept, comprising a first rubella E1 antigen according to the present invention, and a second rubella E1 antigen according to the present invention.

In a further preferred embodiment, the present invention relates to an immunoassay according to the double antigen bridge concept characterized in that a first rubella E1 antigen fusion protein complex is used as capture antigen and a second rubella E1 antigen fusion protein complex is used as detection antigen.

The rubella E1 antigen fusion protein complex, preferable the rubella E1 antigen-chaperone complex as described in the present invention not only bring about the solubility of various proteins that are otherwise difficult to handle, but they also allow for a very advantageous immunoassay according to the double antigen bridge concept.

It is an especially attractive feature of such an immunoassay according to the double antigen bridge concept, that it is now possible to use different chaperones for complex formation with the solid phase bound antigen and for complex formation with the detection antigen, respectively. Such modification of an assay further improves upon the problem of non-specific binding. Antibodies in a sample, which would be reactive to a chaperone and thus might cause a false positive signal, will not form a bridge if different chaperones are used to complex the solid phase antigen and the detection antigen, respectively. Therefore, in this mode of the invention, the likelihood of a positive signal due to non-specific binding is largely reduced. In a preferred embodiment, the present invention therefore relates to an immunoassay according to the double antigen bridge concept which is characterized in that the first chaperone and the second chaperone of a first and a second chaperone-rubella E1 antigen complex differ from each other.

Most of the chaperones that are best characterized have been isolated from *Escherichia coli*, which is widely used in biotechnological research. Since *Escherichia coli* is a widely distributed bacterial species, many mammals have developed antibodies against proteins derived from this bacterium. In order to reduce the likelihood of false positive reactions caused by such antibodies, it is preferred to use at least one PPI chaperone derived from a distinct bacterial species, preferably a thermophilic one. Preferably the chaperone is derived from extremophilic bacteria, especially of the group of bacteria comprising Thermatoga maritima, Aquifex aeolicus and Thermus thermophilus.

The use of a chaperone-antigen complex in an immunoassay in general, and preferably in an immunoassay according to the bridge concept, also provides the possibility to derivatise the chaperone of such a complex and does not require the modification of the antigen itself. It is generally accepted that the modification of a protein by a second chemical moiety, for example, the coupling of a label to that molecule, includes the risk of negatively influencing the polypeptide. For example, the epitope under investigation may be compromised, or non-specific binding may be caused by such labeling. According to the present invention, it is now possible to derivatise specifically the chaperone within a rubella E1 antigen-chaperone complex.

In a preferred embodiment, an immunoassay according to the double antigen bridge concept is further characterized in that the first rubella E1 antigen-chaperone complex used as capture antigen comprises a solid phase binding group.

In a further preferred embodiment, an immunoassay according to the bridge concept is performed, which is further characterized in that the second rubella E1 antigen-chaperone complex used as detection antigen comprises a marker group.

The present invention further relates to the use of at least one antigen of rubella E1 in a diagnostic test for the detection of anti-rubella antibodies as well as further usual additives as required.

A further subject matter of the invention is a reagent kit for the detection of antibodies against rubella, which in addition to the usual test additives for immunoassays, containing at least one antigen of the rubella E1 antigens suitable for specifically binding to rubella antibodies to be determined and eventually carrying a label as well as other usual additives if necessary. In particular the reagent kit contain a rubella E1 antigen and variants of this protein containing the N-terminal region spanning the disulfide bridges bridges Cys 8-Cys 13 and Cys 59-Cys 71, more preferable the disulfide bridges Cys 8-Cys 13 and Cys 59-Cys 71 and Cys 117-Cys 130.

Preferable, the reagent kit contain a rubella E1 antigen and variants of this protein containing the C-terminal region spanning the disulfide bridges Cys 349-Cys 352 and Cys 368-Cys 401, more preferable the combination of the disulfide bridges bridges Cys 225-Cys 235, Cys 349-Cys 352 and Cys 368-Cys 401 or the combination of the disulfide bridges Cys 176-Cys 185, Cys 349-Cys 352 and Cys 368-Cys 401, most preferable the combination of the disulfide bridges Cys 176-Cys 185, Cys 225-Cys 235, Cys 349-Cys 352 and Cys 368-Cys 401.

A further embodiment of the present invention is a reagent kit which contains the rubella E1 antigen and variants of this peptide characterized by lacking at the C-terminal end at least the transmembran region and the anchor segment as well as at least the amino acids 143 to 164, preferably 134 to about 168, and containing at least the region spanning the disulfide bridges Cys 349-Cys 352 and Cys 368-401 whereas the N-terminus (Cys 349) of this region contains additionally at least 15 amino acids and/or the C-terminus (Cys 401) of this region contains additionally at least 8 amino acids of the adjacent rubella E1 antigen sequence.

Furthermore, the N-terminus (Cys 349) of this region contains additionally at least 25, 30, 34 amino acids and/or the C-terminus (Cys 401) of this region contains additionally at least 10, 11, 15, 25, 35 amino acids of the adjacent rubella E1 antigen sequence. The reagent kit contains further the combination of a rubella E1 antigen containing the C-terminal region spanning at least the disulfide bridges Cys 349-Cys 352 and Cys 368-Cys 401, more preferable the combination of the disulfide bridges bridges Cys 225-Cys 235, Cys 349-Cys 352 and Cys 368-Cys 401 or the combination of the disulfide bridges Cys 176-Cys 185, Cys 349-Cys 352 and Cys 368-Cys 401, most preferable the combination of the disulfide bridges Cys 176-Cys 185, Cys 225-Cys 235, Cys 349-Cys 352 and Cys 368-Cys 401 and the N-terminal region spanning at least the disulfide bridges bridges Cys 8-Cys 13 and Cys 59-Cys 71, more preferable the combination of the disulfide bridges Cys 8-Cys 13 and Cys 59-Cys 71 and Cys 117-Cys 130.

In addition, the reagent kit contains control and standard solutions as well as reagents in one or more solutions with the common additives, buffers, salts, detergents, et cetera as used by the average man skilled in the art.

SPECIFIC EMBODIMENTS

EXAMPLE 1

Construction of an Expression Plasmid Comprising Tandem-EcSlyD and the Rubella E1 Ectodomain Fragment E1 (201-432)

On the basis of the pET24a expression plasmid of Novagen (Madison, Wis., USA) the following cloning steps were performed. The vector was digested with Nde I and Xho I and a semi-synthetic cassette comprising tandem SlyD and the rubella E1 fragment 201-432 was inserted. This rubella E1 fragment contains cysteine residues at position of amino acid 349, 352, 368 and 401.

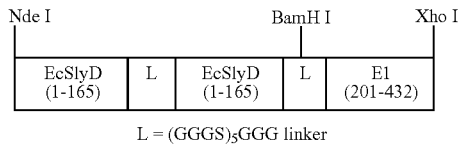

L = (GGGS)$_5$GGG linker (Linker peptide disclosed as SEQ ID NO: 3) The insert of the resulting plasmid was sequenced and found to encode the desired fusion protein. The nucleic acid sequence of the inserted cassette and the amino acid sequence of the resulting fusion protein are shown in the sequence protocol of the present invention.

EXAMPLE 2

Coupled Purification and Refolding of the SS-E1 (201-432) Fusion Protein

E. coli BL21(DE3) cells harboring the expression plasmid were grown in LB medium plus kanamycin (30 μg/ml) to an $OD_{600}$ of 1, and cytosolic overexpression was induced by adding Isopropyl-β-D-Thiogalactosid (IPTG) to a final concentration of 1 mM at a growth temperature of 37° C. 4 hours after induction, cells were harvested by centrifugation (20 min at 5000 ×g), frozen and stored at −20° C. For cell lysis, the frozen pellet was resuspended in 100 mM sodium phosphate pH 8.0, 7.0 M GuHCl, 10 mM imidazole at room temperature and the resulting suspension was stirred to complete cell lysis for two hours. After centrifugation and filtration, the lysate was applied onto a Ni-NTA (nickel-nitrilotriacetate) column pre-equilibrated in the aforementioned lysis buffer. In order to prevent premature disulfide bridging and SS shuffling, 5 mM TCEP was included in the washing buffer as a reducing agent which is compatible with metal chelate columns. After an excessive washing step (>20 column volumes of lysis buffer+TCEP), the chaotropic lysis buffer was displaced by 50 mM sodium phosphate pH 7.8, 100 mM sodium chloride, 5 mM TCEP in order to induce the conformational refolding of the matrix bound protein (at least 10 column volumes of refolding buffer were applied to make sure there was no residual GuHCl in chaotropic concentrations). Subsequently, the oxidative folding (i.e. the oxidative bridging of the cysteine residues) was induced by washing with 50 mM sodium phosphate pH 7.8, 100 mM sodium chloride. Due to the high effective concentration of divalent $Ni^{2+}$ ions, the formation of disulfide bridges within the matrix-bound fusion protein is a very fast process. Prior to elution, the imidazole concentration was raised to 55 mM in order to remove a contaminant protein with an apparent molecular weight of ~50 kDa. The native fusion protein was then eluted by applying an imidazole gradient from 55 mM to 500 mM in 50 mM sodium phosphate pH 7.8, 100 mM sodium chloride. Protein containing fractions were assessed for purity (>95% as judged by SDS-PAGE) and pooled. Finally, the protein was subjected to size exclusion chromatography and the dimer fraction was pooled, concentrated and assessed for its spectroscopic properties.

EXAMPLE 3

Characterization of the Rubella E1 Fusion Protein a. UV-Spectroscopy

The SS-E1(201-432) elutes as a soluble and native-like folded protein. The UV spectra of the recombinantly produced and matrix-refolded fusion protein do not indicate any aggregation tendency. As shown in FIG. 1, the baseline of the UV-absorption spectrum of SS-E1 (201-432) in physiological buffer conditions almost equals the abscissa (beyond 310 nm), thus indicating that there are no light-straying particles resulting from self-association or aggregation phenomena.

FIG. 1: UV spectrum of the fusion protein SS-E1 (201-432) after matrix-assisted refolding and imidazole gradient elution. The spectrum was recorded on a Uvicon XS photometer using a pathlength of 1 cm. Buffer conditions were 50 mM sodium phosphate pH 8.0, 100 mM sodium chloride and ~250 mM imidazole. Using a molar extinction coefficient ε of 48370 $M^{-1}$ $cm^{-1}$ for SS-E1 (201-432), the protein concentration was determined to be 7.25 μM. The shape of the spectrum reflects the solubility of the chaperoned rubella E1 ectodomain fragment (201-432).

b. SDS Gel-Electrophoresis

Figure 2:
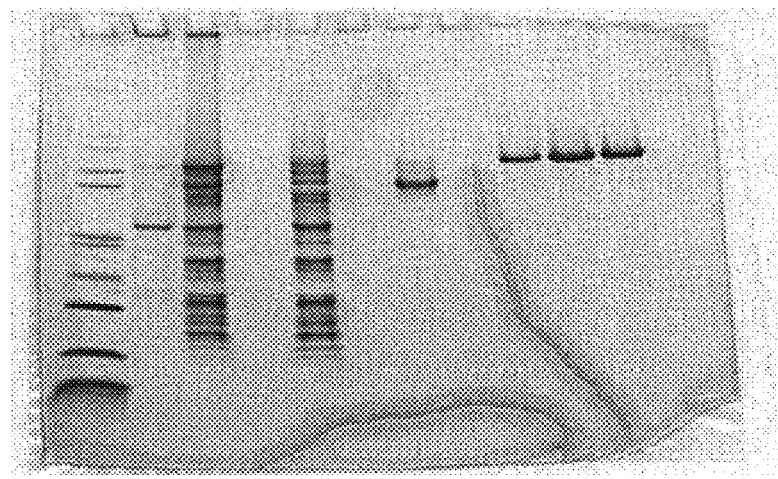
FIG. 2 shows a purification of SS-E1 (201-432) as documented by non-reducing SDS-PAGE. See Example 3b.

The purity of the fusion polypeptide rubella SS-E1 amino acid residues 201-432 was verified by SDS-PAGE (FIG. 2). After a two-step chromatography the purity of the fusion polypeptide exceeds 95%.

FIG. 2: Purification of SS-E1 (201-432) as documented by non reducing SDS-PAGE. The Coomassie-stained gel shows (from left to right) the protein standard M12 from Invitrogen (lane 1), the E. coli chaotropic crude extract (insoluble fraction lane 2, soluble fraction lane 3), the IMAC flowthrough (lane 5), the washing fraction containing a prominent contamination with an apparent molecular mass of ~50 kDa (lane 7) and the SS-E1 (201-432) imidazole elution fractions (lanes 9-11). The purity of the fusion protein exceeds 95% as judged from the SDS-PAGE. There is no indication for mixed disulfides or covalent intermolecular SS adducts. This indicates the quantitative bridging of the cysteines 349 & 352 and of the cysteines 368 & 401, respectively.

c. FPLC Analysis (Fast Protein Liquid Chromatography Analysis)

Besides its antigenicity, the oligomeric state, the solubility and the stability of the SS-E1 fusion protein determine its suitability for diagnostic purposes. In order to elucidate the oligomeric state of the recombinant rubella ectodomain fragment, variants of SS-E1(201-432) differing in the cysteine content were subjected to analytical gel filtration on a Superdex 200 HR 10/30 column. The running buffer was 50 mM sodium phosphate pH 7.5, 100 mM NaCl. 150 µl of the SS-E1 (201-432) solution (protein concentration~1.0 mg/ml) were applied onto the SEC column, and elution was monitored via absorption at 280 nm (FIG. 3).

The outcome of the experiment demonstrates that all SS-E1 (201-432) cysteine variants quantitatively eluted at~12.8 ml, pointing to apparently dimeric fusion proteins. This is in line with the expectation that the introduction of a disulfide bond constrains the polypeptide backbone of the rubella ectodomain and leads to an overall compaction of the molecule. The obvious lack of high molecular associates in the FPLC analysis confirms the results of the SDS-PAGE and corroborates the assumption that the matrix-coupled oxidative refolding of SS-E1 (201-432) yields native-like disulfide bridges which are rather stable and do neither tend to isomerization nor shuffling. The oligomerization of SS-E1 (201-432) is probably mediated by the chaperone fusion partner SlyD, which has been reported to form stable dimers (Mukherjee et al., Biotechnol. Appl. Biochem. (2003) 37, 183-186; Mitterauer et al., Biochem. J. (1999) 342, 33-39).

Figure 3:
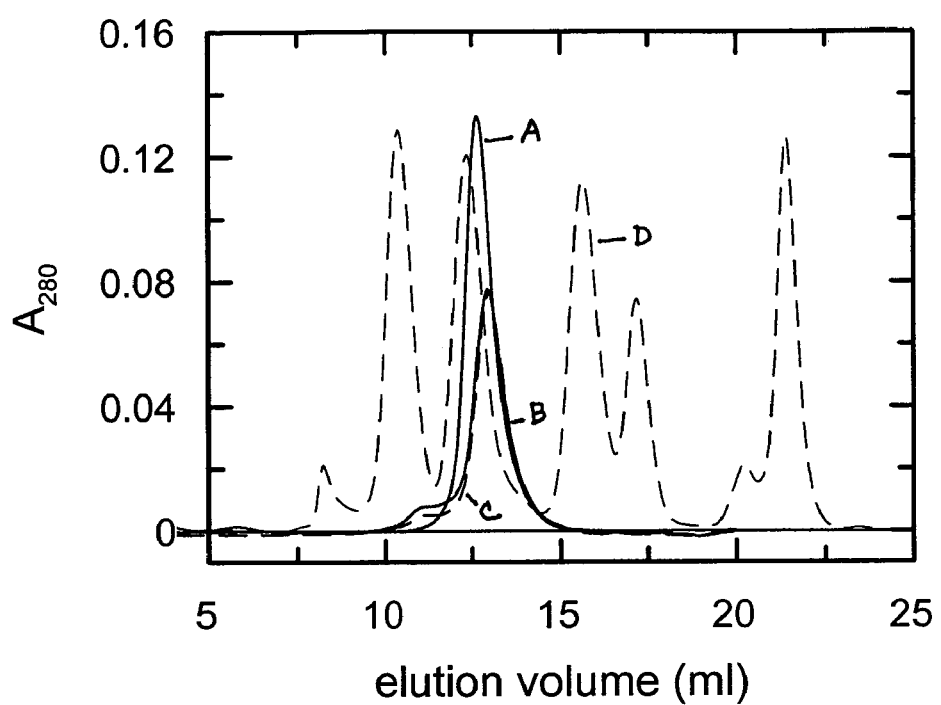
FIG. 3 shows cysteine variants of SS-E1 (201-432) all form soluble dimers when assessed by FPLC analysis. See Example 3c.

FIG. 3: Cysteine variants of SS-E1(201-432) all form soluble apparent dimers when assessed by FPLC analysis. Cysteine-free and disulfide-bridged variants of SS-E1 (201-432) were run on a Superdex 200 HR 10/30 analytical gel filtration column and assessed for their apparent oligomeric state. The running buffer was 50 mM sodium phosphate pH 7.8, 100 mM sodium chloride, 1 mM EDTA, the protein load was~200 µg. Elution was monitored by absorption at 280 nm. The more extended cysteine-free SS-E1 (201-432) elutes at 12.6 ml (A, continuous dark gray line), whereas the more compact double (B, continuous black line) and triple (C, broken black line) disulfide bridge variants elute both at 12.9 ml. The Roche HPLC protein standard (D, broken light gray line) includes β-galactosidase (465 kDa), IgG (150 kDa), Fab (50 kDa), myoglobin (17 kDa) and the dipeptide Gly-Tyr (238 Da).

EXAMPLE 4

Coupling of Biotin and Ruthenium Moieties to SS-E1 (201-432)

The lysine ε-amino groups of the recombinant rubella ectodomains were modified at protein concentrations of~10 mg/ml with N-hydroxy-succinimide activated biotin and ruthenium labels, respectively. The label/protein molar ratio varied from 2:1 to 5:1, depending on the respective fusion protein. The reaction buffer was 150 mM sodium phosphate (pH 8.0), 50 mM NaCl, 1 mM EDTA. The reaction was carried out at room temperature for 15 minutes and stopped by adding buffered L-Lysine to a final concentration of 10 mM. After the coupling reaction, unreacted free label was removed by passing the druce protein conjugate over a gel filtration column (Superdex 200 HI Load).

EXAMPLE 5

Examination of the Immunologiocal Reactivity of the Recombinant Rubella E1 Fusion Protein SS-E1 (aa 201-432) in an Immunodiagnostic Test; Detection of Anti-Rubella IgG Antibodies in Native Sera The immunological reactivity of the different fusion proteins was assessed in an automated ELECSYS 2010 analyzer (Roche Diagnostics GmbH). Measurements were carried out in the double antigen sandwich format. Thereby, the biotin-conjugate (i.e. the capture antigen) is immobilized on the surface of a streptavidin-coated magnetic bead, whereas the detection-antigen bears a complexed ruthenium cation as the signaling moiety. Signal detection in ELECSYS 2010 is based on electrochemoluminiscence.

In the presence of a specific immunoglobulin analyte, the chromogenic ruthenium complex is bridged to the solid phase and emits light at 620 nm after excitation at a platinum electrode. The signal output is in arbitrary light units. Measuring was performed with anti-rubella IgG positive samples from sera collectives of the Bavarian Red Cross.

TABLE 1

Detection of anti-rubella IgG antibodies in native sera by using rubella SS-E1 (aa 201-432) antigen

| Antigen combination | Rubella E1 (Cys-349/Cys-352 + Cys-368/Cys401)-biotin Rubella E1 (Cys-349/Cys-352 + Cys-368/Cys401)-ruthenium | |
|---|---|---|
| cut off* | 2100 | |
| sample | counts | COI |
| Cal 1 | 10908 | 5.19 |
| Cal 2 | 33215 | 15.82 |
| Neg 06020014 | 1481 | 0.71 |
| Neg 06020016 | 1414 | 0.67 |
| BRK 301 | 49160 | 23.41 |
| BRK 302 | 56761 | 27.03 |
| BRK 303 | n.t. | n.t. |
| BRK 304 | n.t. | n.t. |
| BRK 305 | 35019 | 16.68 |
| BRK 306 | 80002 | 38.10 |
| BRK 307 | 60844 | 28.97 |
| BRK 308 | 45472 | 21.65 |
| BRK 309 | 194854 | 92.79 |
| BRK 310 | 201516 | 95.96 |
| BRK 311 | 32427 | 15.44 |
| BRK 312 | n.t. | n.t. |
| BRK 313 | 68884 | 32.80 |
| BRK 314 | n.t. | n.t. |
| BRK 315 | 13663 | 6.51 |
| BRK 316 | 24443 | 11.64 |
| BRK 317 | n.t. | n.t. |
| BRK 318 | n.t. | n.t. |
| BRK 319 | 136838 | 65.16 |
| BRK 321 | 326378 | 155.42 |
| BRK 322 | 177692 | 84.62 |
| BRK 323 | 85215 | 40.58 |
| BRK 324 | 42409 | 20.19 |
| BRK 325 | 17430 | 8.30 |
| BRK 326 | 107751 | 51.31 |
| BRK 327 | 81189 | 38.66 |
| BRK 328 | n.t. | n.t. |
| BRK 329 | n.t. | n.t. |
| BRK 330 | n.t. | n.t. |
| BRK 51 | 264023 | 125.73 |

All sera classified as positive were analysed as being correct. Furthermore, the results reveal a clear discrimination between positive (COI*≧1) and negative (COI*<1) samples.

EXAMPLE 6

Immunological Detection of Anti-rubella IgG Antibodies in Native Sera by using Rubella SS-E1(aa 315-432)-Relevance of Native-like Tertiary Structure for the Immunological Activity Measuring of three different combinations of rubella E1 variants, forming disulfide bridges between cystein 349 and 352, between cystein 349 and cystein 352 as well as between cystein 368 and 401, and between cystein 268 and 401 was conducted. A cystein-free antigen was used in comparison to the above described rubella variants.

Measuring was performed with samples (from WHO standard) and anti-rubella IgG positive samples from sera-collectives of the Bavarian Red Cross. Measurements was carried out in an automated ELECSYS 2010 analyzer (Roche Diagnostics GmbH) using the double antigen sandwich format.

TABLE 2

Detection of anti-rubella IgG antibodies in native sera by using rubella SS-E1 (aa 315-432) antigen

| | | Antigen combination | | |
|---|---|---|---|---|
| | Rubella E1 (Cys-free)-biotin<br>Rubella E1 (Cys-free)-ruthenium | Rubella E1 (Cys-349/Cys-352)-biotin<br>Rubella E1 (Cys-349/Cys-352)-ruthenium | Rubella E1 (Cys-349/Cys-352 + Cys-368/Cys401)-biotin<br>Rubella E1 (Cys-349/Cys-352 + Cys-368/Cys401)-ruthenium | Rubella E1 (Cys-368/Cys-401)-biotin<br>Rubella E1 (Cys-368/Cys-401)-ruthenium |
| | | | cut off* | |
| sample | counts | 1420 counts / COI | 1930 counts / COI | 1199 counts / COI |
|---|---|---|---|---|
| WHO 1 0 IU/ml | 1629 / 0.99 | 1'412 / 0.99 | 1'385 / 0.72 | 1'151 / 0.96 |
| WHO 2 10 IU/ml | 1651 / 1.00 | 1'420 / 1.00 | 1'930 / 1.00 | 1'199 / 1.00 |
| WHO 3 50 IU/ml | 1646 / 1.00 | 1'458 / 1.03 | 4'007 / 2.08 | 1'236 / 1.03 |
| WHO 4 150 IU/ml | 1641 / 0.99 | 1'477 / 1.04 | 8'805 / 4.56 | 1'434 / 1.20 |
| WHO 5 300 IU/ml | 1655 / 1.00 | 1'498 / 1.06 | 15'990 / 8.28 | 1'701 / 1.42 |
| Neg 0602035 | 1602 / 0.97 | 1'413 / 1.00 | n.d. / n.d. | 1'152 / 0.96 |
| Neg 0602036 | 1771 / 1.07 | 1'484 / 1.05 | 1'421 / 0.74 | 1'158 / 0.97 |
| Neg 0602037 | 1563 / 0.95 | 1'392 / 0.98 | 1'359 / 0.70 | 1'165 / 0.97 |
| Neg 0602038 | 1610 / 0.98 | 1'406 / 0.99 | 1'391 / 0.72 | 1'143 / 0.95 |
| BRK 301 | 1691 / 1.02 | 1'494 / 1.05 | 6'723 / 3.48 | 1'505 / 1.25 |
| BRK 302 | 1608 / 0.97 | 1'421 / 1.00 | 7'700 / 3.99 | 1'384 / 1.15 |
| BRK 303 | 1602 / 0.97 | 1'418 / 1.00 | 48'855 / 25.31 | 6'349 / 5.30 |
| BRK 304 | 1957 / 1.19 | 1'699 / 1.20 | 50'481 / 26.15 | 5'709 / 4.76 |
| BRK 305 | 1674 / 1.01 | 1'482 / 1.04 | 5'467 / 2.83 | 1'311 / 1.09 |
| BRK 306 | 1653 / 1.00 | 1'419 / 1.00 | 11'469 / 5.94 | 1'292 / 1.08 |
| BRK 307 | 1616 / 0.98 | 1'402 / 0.99 | 8'572 / 4.44 | 1'525 / 1.27 |
| BRK 308 | 1758 / 1.07 | 1'557 / 1.10 | 6'786 / 3.52 | 1'375 / 1.15 |
| BRK 309 | 1887 / 1.14 | 1'606 / 1.13 | 25'301 / 13.11 | 1'605 / 1.34 |
| BRK 310 | n.t. / n.t. | n.d. / n.d. | n.d. / n.d. | 1'794 / 1.50 |
| BRK 311 | 1689 / 1.02 | 1'483 / 1.04 | 23'529 / 12.19 | 1'232 / 1.03 |
| BRK 312 | 1597 / 0.97 | 1'407 / 0.99 | 4'569 / 2.37 | n.d. / n.d. |
| BRK 313 | 1589 / 0.96 | 1'427 / 1.00 | 9'980 / 5.17 | 1'408 / 1.17 |
| BRK 314 | 1969 / 1.19 | 1'666 / 1.17 | 24'287 / 12.58 | 2'344 / 1.96 |
| BRK 315 | 1621 / 0.98 | 1'397 / 0.98 | 2'911 / 1.51 | 1'149 / 0.96 |
| BRK 316 | 1613 / 0.98 | 1'419 / 1.00 | 3'954 / 2.05 | 1'232 / 1.03 |
| BRK 317 | 1573 / 0.95 | 1'413 / 1.00 | 19'782 / 10.25 | n.d. / n.d. |
| BRK 318 | 1597 / 0.97 | 1'501 / 1.06 | 102'732 / 53.23 | 8'361 / 6.97 |
| BRK 319 | 1625 / 0.98 | 1'419 / 1.00 | 18'070 / 9.36 | 1'508 / 1.26 |
| BRK 321 | 1606 / 0.97 | 1'488 / 1.05 | 41'297 / 21.40 | 1'970 / 1.64 |
| BRK 322 | 1634 / 0.99 | 1'424 / 1.00 | 22'746 / 11.79 | 2'034 / 1.70 |
| BRK 323 | 1567 / 0.95 | 1'397 / 0.98 | 11'705 / 6.06 | 1'429 / 1.19 |
| BRK 324 | 1621 / 0.98 | 1'409 / 0.99 | 6'509 / 3.37 | 1'165 / 0.97 |
| BRK 325 | 1617 / 0.98 | 1'433 / 1.01 | 3'306 / 1.71 | 2'755 / 2.30 |
| BRK 326 | 1588 / 0.96 | 1'425 / 1.00 | 14'232 / 7.37 | 2'329 / 1.94 |
| BRK 327 | 1611 / 0.98 | 1'432 / 1.01 | 11'226 / 5.82 | 1'554 / 1.30 |
| BRK 328 | 1602 / 0.97 | 1'405 / 0.99 | 26'680 / 13.82 | 1'537 / 1.28 |
| BRK 329 | 1681 / 1.02 | 1'480 / 1.04 | 22'449 / 11.63 | 1'174 / 0.98 |
| BRK 330 | 1644 / 1.00 | 1'450 / 1.02 | 2'066 / 1.07 | 1'232 / 1.03 |
| BRK 51 | 1637 / 0.99 | 1'423 / 1.00 | 31'886 / 16.52 | 2'358 / 1.97 |

Comparison of the different variants differing in the formation of disulfide bridges, demonstrate the immunoreactivity of rubella SS-E1 (aa 315-432). The disulfide bridges between cysteine 349 and cysteine 352 and cysteine 368 and cysteine 401 of rubella SS-E1 (aa 315-432) are correctly formed. All sera classified as positive were analysed as being correct. Furthermore, the results reveal a clear discrimination between positive (COI*≧1) and negative (COJ*<1) samples.

EXAMPLE 7

Immunological Detection of Anti-rubella IgG Antibodies in Native Sera by Using Rubella SS-E1 (aa 315-412) and rubella SS-E1 (aa 201-432)

Measuring was performed with samples anti-rubella IgG positive samples from sera-collectives of the Bavarian Red Cross. Measurements was carried out in an automated ELECSYS 2010 analyzer (Roche Diagnostics GmbH) using the double antigen sandwich format.

TABLE 3

Detection of anti-rubella IgG antibodies in native sera by using rubella SS-E1 (aa 315-412) and rubella SS-E1 (aa 201-432) antigen

| Antigen combination | Rubella E1 (315-412, Cys-349/Cys-352 + Cys 368/Cys-401)-biotin Rubella E1 (315-412, Cys-349/Cys-352 + Cys 368/Cys-401)-ruthenium | | Rubella E1 (201-432, Cys-349/Cys-352 + Cys 368/Cys-401)-biotin Rubella E1 (201-432, Cys-349/Cys-352 + Cys 368/Cys-401)-ruthenium | |
|---|---|---|---|---|
| | Counts | | Counts | |
| Cal 1 | 750 | | 701 | |
| Cal 2 | 23528 | | 25666 | |
| | Cut-off* 2353 counts | | Cut-off* 2567 counts | |
| | Counts | COI | Counts | COI |
| Rub IgG Cal 1 | 771 | 0.33 | 707 | 0.28 |
| Rub IgG Cal 1 | 729 | 0.31 | 696 | 0.27 |
| Rub IgG Cal 2 | 23581 | 10.02 | 25728 | 10.02 |
| Rub IgG Cal 2 | 23475 | 9.98 | 25604 | 9.97 |
| Rub IgG Crt 1 | 738 | 0.31 | 722 | 0.28 |
| Rub IgG Crt 2 | 11018 | 4.68 | 13459 | 5.24 |
| BRK(12/04)_231 | 143604 | 61.03 | 167993 | 65.44 |
| BRK(12/04)_232 | 44207 | 18.79 | 52976 | 20.64 |

TABLE 3-continued

Detection of anti-rubella IgG antibodies in native sera by using rubella SS-E1 (aa 315-412) and rubella SS-E1 (aa 201-432) antigen

| BRK(12/04)_233 | 6369 | 2.71 | 7397 | 2.88 |
|---|---|---|---|---|
| BRK(12/04)_234 | 25172 | 10.7 | 29834 | 11.62 |
| BRK(12/04)_235 | 14968 | 6.36 | 19555 | 7.62 |
| BRK(12/04)_236 | 21997 | 9.35 | 26676 | 10.39 |
| BRK(12/04)_237 | 6224 | 2.65 | 9190 | 3.58 |
| BRK(12/04)_238 | 213025 | 90.53 | 249577 | 97.22 |
| BRK(12/04)_239 | 6041 | 2.57 | 7482 | 2.91 |
| BRK(12/04)_240 | 7021 | 2.98 | 9036 | 3.52 |
| BRK(12/04)_241 | 22032 | 9.36 | 30673 | 11.95 |
| BRK(12/04)_242 | 16693 | 7.09 | 22727 | 8.85 |
| BRK(12/04)_243 | 20452 | 8.69 | 27408 | 10.68 |
| BRK(12/04)_244 | 42915 | 18.24 | 57870 | 22.54 |
| BRK(12/04)_245 | 71706 | 30.47 | 79516 | 30.98 |
| BRK(12/04)_246 | 81777 | 34.75 | 93339 | 36.36 |
| BRK(12/04)_247 | 27047 | 11.49 | 37747 | 14.7 |
| BRK(12/04)_248 | 713 | 0.30 | 663 | 0.26 |
| BRK(12/04)_249 | 8450 | 3.59 | 11039 | 4.3 |
| BRK(12/04)_250 | 14114 | 6.0 | 16071 | 6.26 |
| BRK(12/04)_251 | 35197 | 14.96 | 44403 | 17.3 |
| BRK(12/04)_252 | 27067 | 11.5 | 32125 | 12.51 |
| BRK(12/04)_253 | 23219 | 9.87 | 29399 | 11.45 |
| BRK(12/04)_254 | 60055 | 25.52 | 74010 | 28.83 |
| BRK(12/04)_255 | 2716 | 1.15 | 3193 | 1.24 |
| BRK(12/04)_256 | 2900 | 1.23 | 3703 | 1.44 |
| BRK(12/04)_257 | 6692 | 2.84 | 6784 | 2.64 |
| BRK(12/04)_258 | 68138 | 28.96 | 75097 | 29.25 |
| BRK(12/04)_259 | 436405 | 185.47 | 572054 | 222.85 |
| BRK(12/04)_260 | 726 | 0.31 | 689 | 0.27 |

Comparison of the different variants differing in length demonstrates a comparable immunoreactivity of both rubella SS-E1 (aa 315-412) and rubella SS-E1 (aa 201-432). The disulfide bridges between cysteine 349 and cysteine 352 and cysteine 368 and cysteine 401 are correctly formed for both variants. All sera classified as positive were analysed as being correct. Furthermore, the results reveal a clear discrimination between positive (COI*≧1) and negative (COI*<1) samples.

Further Descriptions to the Tables

The term "cut-off" is a signal to discriminate between positive and negative results, i.e. "signal≧cut-off" is for positive samples, "signal<cut-off" is for negative samples.

The term "COI" is defined as the cut-off index. The COI=signal of sample/signal at cut-off, i.e. COI≧1 for positive samples, COI<1 for negative samples.

What is claimed is:

1. A soluble rubella E1 antigen comprising amino acids 334-409 of the native rubella E1 peptide (SEQ ID NO: 4), wherein a disulfide bridge is formed between Cys 349 and Cys 352 and a second disulfide bridge is formed between Cys 368 and Cys 401, with the proviso that said antigen lacks amino acids 143 to 164 and 453 to 481 of the native rubella E1 peptide (SEQ ID NO: 4).

2. The soluble rubella E1 antigen of claim 1 wherein the antigen comprises a peptide selected from the group consisting of amino acids 169-432, amino acids 201-432, amino acids 315-412 and amino acids 315-432.

3. The soluble rubella E1 antigen of claim 1 wherein the antigen further comprises amino acids 8-71 of (SEQ ID NO: 4), wherein a disulfide bridge is formed between Cys 8 and Cys 13 and a second disulfide bridge is formed between Cys 59 and Cys 71.

4. The soluble rubella E1 antigen of claim 2 wherein the antigen further comprises amino acids 8-71 of (SEQ ID NO: 4), wherein a disulfide bridge is formed between Cys 8 and Cys 13 and a second disulfide bridge is formed between Cys 59 and Cys 71.

5. The soluble rubella E1 antigen of claim 1 wherein the antigen further comprises an additional amino acid sequence of (SEQ ID NO: 4) wherein the additional sequence is selected from the group consisting of 8-71, 117-130, and 225-235.

6. The soluble rubella E1 antigen of claim 5 wherein the antigen comprises amino acids 8-71, 117-130, and 225-235 of SEQ ID NO: 4 with the proviso that the antigen lacks amino acids 143 to 164 and 438-481 of SEQ ID NO: 4.

7. The soluble rubella E1 antigen of claim 1 with the proviso that the antigen lacks amino acids 438-452 of SEQ ID NO: 4.

8. The soluble rubella E1 antigen of claim 6 wherein the antigen further comprises amino acids 176-185 of SEQ ID NO: 4, wherein a disulfide bridge is formed between Cys 176 and Cys 185.

9. The soluble rubella E1 antigen of claim 1 wherein the antigen comprises a peptide sequence of SEQ ID NO: 4 selected from the group consisting of amino acids 309-419, amino acids 309-420, amino acids 309-424, amino acids 309-434, amino acids 309-444, amino acids 304-419, amino acids 304-420, amino acids 304-424, amino acids 304-434, amino acids 304-444, amino acids 300-419, amino acids 300-419, amino acids 300-424, amino acids 300-434, and amino acids 300-444.

10. The soluble rubella E1 antigen of claim 1 wherein the rubella E1 antigen is fused with a peptidyl-prolyl-isomerase class chaperone.

11. The soluble rubella E1 antigen of claim 10 wherein the chaperone is a FKBP chaperone selected from the group consisting of FkpA, SlyD and trigger factor.

12. The soluble rubella E1 antigen of claim 1 wherein the antigen comprises the sequence of SEQ ID NO: 2.

13. A method for detecting anti-rubella antibodies of IgG and/or IgM subclass in a sample, said method comprising contacting the sample with the rubella E1 antigen of claim 1, wherein the antigen serves as a capture reagent or binding partner for the antibodies, wherein said antigen is labeled;

removing labeled antigen that is not bound to anti-rubella antibodies of IgG and/or IgM subclass; and detecting any remaining labeled antigen as an indicator of the presence of anti-rubella antibodies of IgG and/or IgM subclass.

14. An immunoassay for detecting anti-rubella antibodies according to the double antigen bridge concept, said method comprising:

providing a first rubella E1 antigen according to claim 1, linked to a solid support;

contacting said first rubella E1 antigen of claim 1 with a sample to form an antibody/capture composition;

contacting the antibody/capture composition with a second rubella E1 antigen wherein said second rubella E1 antigen is labeled;

removing unbound labeled second rubella E1 antigen; and detecting any remaining labeled second rubella E1 antigen as an indicator of the presence of anti-rubella antibodies.

15. A reagent kit for the detection of anti-rubella antibodies, said kit comprising the rubella E1 antigen of claim 1.

16. The immunoassay of claim 14 wherein each of said first and second rubella E1 antigen is fused with a peptidyl-prolyl-isomerase class chaperone.

* * * * *

SEQUENCE LISTING

<160> NUMBER OF SEQ ID NOS: 3

<210> SEQ ID NO 1
<211> LENGTH: 1965
<212> TYPE: DNA
<213> ORGANISM: Artificial Sequence
<220> FEATURE:
<223> OTHER INFORMATION: Description of Artificial Sequence: Synthetic
      Rubella virus E1 chaperone fusion sequence

<400> SEQUENCE: 1

```
gaattgtgag cggataacaa ttcccctcta gaaataattt tgtttaactt taagaaggag      60
atatacatat gaaagtagca aaagacctgg tggtcagcct ggcctatcag gtacgtacag     120
aagacggtgt gttggttgat gagtctccgg tgagtgcgcc gctggactac ctgcatggtc     180
```

-continued

```
acggttccct gatctctggc ctggaaacgg cgctggaagg tcatgaagtt ggcgacaaat    240
ttgatgtcgc tgttggcgcg aacgacgctt acggtcagta cgacgaaaac ctggtgcaac    300
gtgttcctaa agacgtattt atgggcgttg atgaactgca ggtaggtatg cgtttcctgg    360
ctgaaaccga ccagggtccg gtaccggttg aaatcactgc ggttgaagac gatcacgtcg    420
tggttgatgg taaccacatg ctggccggtc agaacctgaa attcaacgtt gaagttgtgg    480
cgattcgcga agcgactgaa gagaactgg ctcatggtca cgttcacggc gcgacgatc     540 accaccacga tcacgaccac gacggtggcg gttccggcgg tggctctggt ggcggatccg    600
gcggaggctc tggggcgga tcaggcgtg aaaggtcgc gaaagatctc gtagtgagcc      660
tcgcttacca agtgcgcact gaggatgggg ttctggtaga cgaatcaccc gtatcggcac    720
cgctcgatta tttgcacggc catggtagcc taattagtgg tttagagaca gcacttgagg    780
gacacgaggt cggtgataag ttcgacgttg cagtgggagc taatgatgcc tatgggcaat    840
atgatgagaa tctcgttcag cgcgtgccga aggatgtgtt catgggtgta gacgagctcc    900
aagtgggcat gcggtttctt gccgagacgg atcaaggccc tgtgccagtc gagattaccg    960
cagtggagga tgaccatgtt gtcgtggacg gaaatcacat gttagcggga caaaatttga   1020
aatttaatgt cgaggtcgtc gctatccgtg aggccaccga agaagagctt gcacacggcc   1080
atgtccatgg tgcccatgac catcaccatg accatgatca tgatggcggt gggtcgggtg   1140
ggggaagtgg gggtggatcc ggtggcggtt ccggcggtgg ctctggtggc ggtggtgacc   1200
tggttgaata catcatgaac tacaccggta accagcagtc ccgttggggt ctgggttccc   1260
cgaacgctca cggtccggac tgggcttccc cggttgctca gcgtcactcc ccggacgctt   1320
cccgtctggt tggtgctacc ccggaacgtc cgcgtctgcg tctggttgac gctgacgacc   1380
cgctgctgcg taccgctccg ggtccgggtg aagtttgggt taccccggtt atcggttccc   1440
aggctcgtaa agctggtctg cacatccgtc tggtccgta cggtcacgct accgttgaaa    1500
tgccggaatg gattcacgct cacaccacct ccgacccgtg gctgccgccg ggtccgctgg   1560
gtctgaaatt caaaaccgtt cgtccggttg ctctgccgcg tgctctggct ccgccgcgta   1620
acgttcgtgt taccggttgc taccagtgtg gtaccccggc tctggttgaa ggtctggctc   1680
cgggtggtgg taactgccac ctgaccgtta acggtgaaga cgttggtgcc ttcccaccgg   1740
gtaaattcgt taccgctgct ctgctgaaca ccccgccgcc gtaccaggtt tcctgcggtg   1800
gtgaatccga ccgtgcttcc gctcgtgtta tcgacccggc tgctcagtcc ttcaccggtg   1860
ttgtttacgg tacccacacc accgctgttc tcgagcacca ccaccaccac cactgagatc   1920
cggctgctaa caaagcccga aggaagctg agttggctgc tgcca                    1965
```

<210> SEQ ID NO 2
<211> LENGTH: 615
<212> TYPE: PRT
<213> ORGANISM: Artificial Sequence
<220> FEATURE:
<223> OTHER INFORMATION: Description of Artificial Sequence: Synthetic
      Rubella virus E1 chaperone fusion protein

<400> SEQUENCE: 2

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

```
Leu Glu Gly His Glu Val Gly Asp Lys Phe Asp Val Ala Val Gly Ala
 50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
            115                 120                 125

Asn Leu Lys Phe Asn Val Glu Val Ala Ile Arg Glu Ala Thr Glu
130                 135                 140

Glu Glu Leu Ala His Gly His Val His Gly Ala His Asp His His
145                 150                 155                 160

Asp His Asp His Asp Gly Gly Ser Gly Gly Gly Ser Gly Gly Gly
                165                 170                 175

Ser Gly Gly Gly Ser Gly Gly Ser Gly Gly Gly Lys Val Ala Lys
            180                 185                 190

Asp Leu Val Val Ser Leu Ala Tyr Gln Val Arg Thr Glu Asp Gly Val
            195                 200                 205

Leu Val Asp Glu Ser Pro Val Ser Ala Pro Leu Asp Tyr Leu His Gly
210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
            275                 280                 285

Gln Gly Pro Val Pro Val Glu Ile Thr Ala Val Glu Asp Asp His Val
290                 295                 300

Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His Asp His Asp His Asp
            340                 345                 350

Gly Gly Gly Ser Gly Gly Gly Ser Gly Gly Gly Ser Gly Gly Gly Ser
            355                 360                 365

Gly Gly Gly Ser Gly Gly Gly Asp Leu Val Glu Tyr Ile Met Asn
            370                 375                 380

Tyr Thr Gly Asn Gln Gln Ser Arg Trp Gly Leu Gly Ser Pro Asn Ala
385                 390                 395                 400

His Gly Pro Asp Trp Ala Ser Pro Val Ala Gln Arg His Ser Pro Asp
                405                 410                 415

Ala Ser Arg Leu Val Gly Ala Thr Pro Glu Arg Pro Arg Leu Arg Leu
            420                 425                 430

Val Asp Ala Asp Asp Pro Leu Leu Arg Thr Ala Pro Gly Pro Gly Glu
            435                 440                 445

Val Trp Val Thr Pro Val Ile Gly Ser Gln Ala Arg Lys Ala Gly Leu
            450                 455                 460
```

```
His Ile Arg Ala Gly Pro Tyr Gly His Ala Thr Val Glu Met Pro Glu
465                 470                 475                 480

Trp Ile His Ala His Thr Thr Ser Asp Pro Trp Leu Pro Pro Gly Pro
                485                 490                 495

Leu Gly Leu Lys Phe Lys Thr Val Arg Pro Val Ala Leu Pro Arg Ala
            500                 505                 510

Leu Ala Pro Pro Arg Asn Val Arg Val Thr Gly Cys Tyr Gln Cys Gly
            515                 520                 525

Thr Pro Ala Leu Val Glu Gly Leu Ala Pro Gly Gly Gly Asn Cys His
        530                 535                 540

Leu Thr Val Asn Gly Glu Asp Val Gly Ala Phe Pro Pro Gly Lys Phe
545                 550                 555                 560

Val Thr Ala Ala Leu Leu Asn Thr Pro Pro Pro Tyr Gln Val Ser Cys
                565                 570                 575

Gly Gly Glu Ser Asp Arg Ala Ser Ala Arg Val Ile Asp Pro Ala Ala
            580                 585                 590

Gln Ser Phe Thr Gly Val Val Tyr Gly Thr His Thr Thr Ala Val Leu
        595                 600                 605

Glu His His His His His His
    610             615

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Ser Gly Gly Gly Ser Gly Gly Gly Ser Gly Gly Gly Ser
1               5                   10                  15

Gly Gly Gly Ser Gly Gly Gly
            20
```